United States Patent
Levy et al.

(10) Patent No.: US 8,741,940 B2
(45) Date of Patent: Jun. 3, 2014

(54) MICROBICIDAL COMPOSITION

(75) Inventors: Richard Levy, Valbonne (FR); Megan Anne Diehl, Line Lexington, PA (US); Dolores Ann Shaw, Collegeville, PA (US); Eileen Fleck Warwick, Lansdale, PA (US)

(73) Assignee: Rohm and Haas Company, Philadelphia, PA (US)

( * ) Notice: Subject to any disclaimer, the term of this patent is extended or adjusted under 35 U.S.C. 154(b) by 904 days.

(21) Appl. No.: 11/529,199

(22) Filed: Sep. 28, 2006

(65) Prior Publication Data

US 2007/0078118 A1    Apr. 5, 2007

(30) Foreign Application Priority Data

Oct. 4, 2005 (EP) .................................... 05292073

(51) Int. Cl.
*A61K 31/425* (2006.01)
*A01N 43/80* (2006.01)
*A01N 25/00* (2006.01)
*A61K 31/428* (2006.01)

(52) U.S. Cl.
CPC ........... *A61K 31/428* (2013.01); *A61K 2300/00* (2013.01); *A01N 43/80* (2013.01); *A01N 2300/00* (2013.01)
USPC ......................................... 514/373; 424/405

(58) Field of Classification Search
CPC . A61K 2300/00; A61K 31/428; A01N 43/80; A01N 2300/00
USPC .......................................... 514/373; 424/405
See application file for complete search history.

(56) References Cited

U.S. PATENT DOCUMENTS

| | | | |
|---|---|---|---|
| 3,970,755 A | 7/1976 | Gazzard et al. | |
| 4,964,892 A | 10/1990 | Hsu | |
| 5,147,884 A | 9/1992 | Diehl et al. | |
| 6,114,366 A | 9/2000 | Lutz et al. | |
| 6,133,300 A | 10/2000 | Smith et al. | |
| 6,482,814 B1 | 11/2002 | Bath et al. | |
| 2002/0098211 A1* | 7/2002 | Cupferman et al. | 424/401 |
| 2002/0164266 A1 | 11/2002 | Wachtler et al. | |
| 2003/0199490 A1 | 10/2003 | Antoni-Zimmermann et al. | |
| 2004/0014799 A1 | 1/2004 | Antoni-Zimmermann et al. | |
| 2005/0271595 A1* | 12/2005 | Brown | 424/10.1 |

FOREIGN PATENT DOCUMENTS

| | | | |
|---|---|---|---|
| EP | 0375264 | | 6/1990 |
| EP | 0787430 | | 8/1997 |
| EP | 1084619 | | 3/2001 |
| EP | 1245153 | * | 3/2002 |
| EP | 1245153 | | 10/2002 |
| EP | 1332675 | | 8/2003 |
| EP | 1462003 | | 9/2004 |
| GB | 1461909 | | 1/1977 |
| GB | 1531431 | | 11/1978 |
| JP | 10-298012 | * | 11/1998 |
| JP | 10298012 | | 11/1998 |
| JP | 11071211 | | 3/1999 |
| JP | 11130604 | | 6/1999 |
| JP | 2000191412 | | 7/2000 |
| JP | 2001302418 A | * | 10/2001 |
| JP | 2003192507 | | 7/2003 |
| JP | 2003267806 | | 9/2003 |
| JP | 2004238338 | | 8/2004 |
| JP | 2005089348 | | 4/2005 |
| JP | 2006-328007 | | 12/2006 |

OTHER PUBLICATIONS

JP 2001302418 machine translation.*
JP 10-298012 Machine translation.*
Siqueira et al. "Antibactetrial Effects of endodontic irrigants on black-pigmented Gram-negative anaerobes and facultative bacteria," Journal of Endodontics, 1998, vol. 24, No. 6, pp. 414-416.*
John Payne, "Responding to the Consumer's Desire for Improved Hygiene With Antibacterial Plastics", Polymers and Polymer Composites, (2004) vol. 12, No. 2, pp. 135-142.

* cited by examiner

*Primary Examiner* — Shengjun Wang
(74) *Attorney, Agent, or Firm* — Kenneth Crimaldi

(57) ABSTRACT

Synergistic microbicidal compositions containing N-(n-butyl)-1,2-benzisothiazolin-3-one or N-methyl-1,2-benzisothiazolin-3-one.

3 Claims, No Drawings

MICROBICIDAL COMPOSITION

CROSS REFERENCE TO RELATED PATENT APPLICATIONS

This patent application claims the benefit of the earlier filed European Patent application serial number 05292073.3 filed on Oct. 4, 2005 under 37 CFR 1.55(a).

This invention relates to a synergistic combination of selected microbicides having greater activity than would be observed for the individual microbicides.

In some cases, commercial microbicides cannot provide effective control of microorganisms, even at high use concentrations, due to weak activity against certain types of microorganisms, e.g., those resistant to some microbicides, or due to aggressive environmental conditions. Combinations of different microbicides are sometimes used to provide overall control of microorganisms in a particular end use environment. For example, U.S. Pat. App. Pub. No. 2004/0014799 discloses a synergistic combination of N-(n-butyl)-1,2-benzisothiazolin-3-one (BBIT) and 2-methyl-4-isothiazolin-3-one (MI) over the limited range of ratios of BBIT to MI of 10:1 to 1.67:1. However, there is a need for additional combinations of microbicides having enhanced activity against various strains of microorganisms to provide effective control of the microorganisms. Moreover, there is a need for combinations containing lower levels of individual microbicides for environmental and economic benefit. The problem addressed by this invention is to provide such additional combinations of microbicides.

STATEMENT OF THE INVENTION

The present invention is directed to a microbicidal composition comprising: (a) N-(n-butyl)-1,2-benzisothiazolin-3-one; and (b) at least one microbicide selected from among benzalkonium chloride, benzethonium chloride, benzyl alcohol, benzisothiazolinone, 2-bromo-2-nitropropane-1,3-diol, butylene glycol, caprylyl glycol, chlorphenesin, 1,3-dimethylol-5,5-dimethyl hydantoin, dithio-2,2'-bis(N-methylbenzamide), ethylenediamine tetraacetic acid or its salts, ethylparaben, hexamidine diisethionate, hexetidine, methylparaben, phenoxyethanol, linoleamidopropyl PG-dimonium chloride phosphate, cocamidopropyl PG-dimonium chloride phosphate, propylparaben, sorbic acid or its salts, 1-(3-chloroallyl)-3,5,7-triaza-1-azoniaadamantane chloride, dehydroacetic acid or its salts, benzoic acid or its salts, and citric acid or its salts.

The present invention is further directed to a microbicidal composition comprising: (a) N-methyl-1,2-benzisothiazolin-3-one; and (b) at least one microbicide selected from among N-(n-butyl)-1,2-benzisothiazolin-3-one, benzalkonium chloride, benzethonium chloride, benzyl alcohol, benzisothiazolinone, 2-bromo-2-nitropropane-1,3-diol, butylene glycol, caprylyl glycol, chlorphenesin, dithio-2,2'-bis(N-methylbenzamide), ethylenediamine tetraacetic acid or its salts, ethylparaben, hexamidine diisethionate, hexitidine, methylparaben, phenoxyethanol, linoleamidopropyl PG-dimonium chloride phosphate, cocamidopropyl PG-dimonium chloride phosphate, sorbic acid or its salts, propylparaben, 1-(3-chloroallyl)-3,5,7-triaza-1-azoniaadamantane chloride, dehydroacetic acid or its salts, benzoic acid or its salts, citric acid or its salts, and zinc pyrithione.

DETAILED DESCRIPTION OF THE INVENTION

"BBIT" is N-(n-butyl)-1,2-benzisothiazolin-3-one. "EDTA" is ethylenediamine tetraacetic acid. "MBIT" is N-methyl-1,2-benzisothiazolin-3-one.

As used herein, the following terms have the designated definitions, unless the context clearly indicates otherwise. The term "microbicide" refers to a compound capable of killing, inhibiting the growth of or controlling the growth of microorganisms at a locus; microbicides include bactericides, fungicides and algaecides. The term "microorganism" includes, for example, fungi (such as yeast and mold), bacteria and algae. The term "locus" refers to an industrial system or product subject to contamination by microorganisms. The following abbreviations are used throughout the specification: ppm=parts per million by weight (weight/weight), mL=milliliter, ATCC=American Type Culture Collection, MBC=minimum biocidal concentration, and MIC=minimum inhibitory concentration. Unless otherwise specified, temperatures are in degrees centigrade (° C.), and references to percentages (%) are by weight. Amounts of organic microbicides are given on an active ingredient basis in ppm (w/w).

The compositions of the present invention unexpectedly have been found to provide enhanced microbicidal efficacy at a combined active ingredient level lower than that of the individual microbicides. In one embodiment of the invention, those antimicrobial compositions which contain halogenated 3-isothiazolones contain relatively low levels thereof, preferably no more than 100 ppm, more preferably no more than 500 ppm, more preferably no more than 100 ppm, and most preferably no more than 50 ppm. Concentrations of halogenated 3-isothiazolones in the composition of this invention are based on the total weight of active ingredients in the composition, i.e., the microbicides exclusive of any amounts of solvents, carriers, dispersants, stabilizers or other materials which may be present. In one embodiment of the invention, the antimicrobial composition contains less than 1000 ppm of 5-chloro-2-methyl-4-isothiazolin-3-one, more preferably no more than 500 ppm, more preferably no more than 100 ppm, and most preferably no more than 50 ppm.

In one embodiment of the invention, the antimicrobial composition comprises N-(n-butyl)-1,2-benzisothiazolin-3-one and benzalkonium chloride. Preferably, a weight ratio of N-(n-butyl)-1,2-benzisothiazolin-3-one to benzethonium chloride is from 1:0.1 to 1:30, more preferably from 1:0.3 to 1:20.

In one embodiment of the invention, the antimicrobial composition comprises N-(n-butyl)-1,2-benzisothiazolin-3-one and benzethonium chloride. Preferably a weight ratio of N-(n-butyl)-1,2-benzisothiazolin-3-one to benzethonium chloride is from 1:0.02 to 1:1.5, more preferably from 1:0.01 to 1:1.

In one embodiment of the invention, the antimicrobial composition comprises N-(n-butyl)-1,2-benzisothiazolin-3-one and benzyl alcohol. Preferably, a weight ratio of N-(n-butyl)-1,2-benzisothiazolin-3-one to benzyl alcohol is from 1:1 to 1:1000, more preferably from 1:2 to 1:800, more preferably from 1:3 to 1:800.

In one embodiment of the invention, the antimicrobial composition comprises N-(n-butyl)-1,2-benzisothiazolin-3-one and 1,2-benzisothiazolin-3-one. Preferably, a weight ratio of N-(n-butyl)-1,2-benzisothiazolin-3-one to 1,2-benzisothiazolin-3-one is from 1:0.02 to 1:20, more preferably from 1:0.02 to 1:16.

In one embodiment of the invention, the antimicrobial composition comprises N-(n-butyl)-1,2-benzisothiazolin-3-one and 2-bromo-2-nitropropane-1,3-diol. Preferably, a weight ratio of N-(n-butyl)-1,2-benzisothiazolin-3-one to 2-bromo-2-nitropropane-1,3-diol is from 1:0.01 to 1:500.

In one embodiment of the invention, the antimicrobial composition comprises N-(n-butyl)-1,2-benzisothiazolin-3-one and butylene glycol. Preferably, a weight ratio of N-(n- butyl)-1,2-benzisothiazolin-3-one to butylene glycol is from 1:1 to 1:5000, more preferably from 1:3 to 1:5000.

In one embodiment of the invention, the antimicrobial composition comprises N-(n-butyl)-1,2-benzisothiazolin-3-one and caprylyl glycol. Preferably, a weight ratio of N-(n-butyl)-1,2-benzisothiazolin-3-one to caprylyl glycol is from 1:1 to 1:1000, more preferably from 1:3 to 1:1000.

In one embodiment of the invention, the antimicrobial composition comprises N-(n-butyl)-1,2-benzisothiazolin-3-one and chlorphenesin. Preferably, a weight ratio of N-(n-butyl)-1,2-benzisothiazolin-3-one to chlorphenesin is from 1:0.5 to 1:700, more preferably from 1:1 to 1:500.

In one embodiment of the invention, the antimicrobial composition comprises N-(n-butyl)-1,2-benzisothiazolin-3-one and 1,3-dimethylol-5,5-dimethylhydantoin. Preferably, a weight ratio of N-(n-butyl)-1,2-benzisothiazolin-3-one to 1,3-dimethylol-5,5-dimethylhydantoin is from 1:0.02 to 1:200, more preferably from 1:0.06 to 1:160.

In one embodiment of the invention, the antimicrobial composition comprises N-(n-butyl)-1,2-benzisothiazolin-3-one and dithio-2,2'-bis(N-methylbenzamide). Preferably, a weight ratio of N-(n-butyl)-1,2-benzisothiazolin-3-one to dithio-2,2'-bis(N-methylbenzamide) is from 1:0.02 to 1:160.

In one embodiment of the invention, the antimicrobial composition comprises N-(n-butyl)-1,2-benzisothiazolin-3-one and EDTA or its salts, preferably EDTA. Preferably, a weight ratio of N-(n-butyl)-1,2-benzisothiazolin-3-one to EDTA or its salts is from 1:1 to 1:500, more preferably from 1:3 to 1:500.

In one embodiment of the invention, the antimicrobial composition comprises N-(n-butyl)-1,2-benzisothiazolin-3-one and ethylparaben. Preferably, a weight ratio of N-(n-butyl)-1,2-benzisothiazolin-3-one to ethylparaben is from 1:1 to 1:200, more preferably from 1:2 to 1:200.

In one embodiment of the invention, the antimicrobial composition comprises N-(n-butyl)-1,2-benzisothiazolin-3-one and hexamidine diisethionate. Preferably, a weight ratio of N-(n-butyl)-1,2-benzisothiazolin-3-one to hexamidine diisethionate is from 1:0.02 to 1:3.

In one embodiment of the invention, the antimicrobial composition comprises N-(n-butyl)-1,2-benzisothiazolin-3-one and hexetidine. Preferably, a weight ratio of N-(n-butyl)-1,2-benzisothiazolin-3-one to hexetidine is from 1:0.02 to 1:40.

In one embodiment of the invention, the antimicrobial composition comprises N-(n-butyl)-1,2-benzisothiazolin-3-one and methylparaben. Preferably, a weight ratio of N-(n-butyl)-1,2-benzisothiazolin-3-one to methylparaben is from 1:0.2 to 1:250, more preferably from 1:0.5 to 1:240.

In one embodiment of the invention, the antimicrobial composition comprises N-(n-butyl)-1,2-benzisothiazolin-3-one and phenoxyethanol. Preferably, a weight ratio of N-(n-butyl)-1,2-benzisothiazolin-3-one to phenoxyethanol is from 1:0.5 to 1:800, more preferably from 1:1 to 1:800.

In one embodiment of the invention, the antimicrobial composition comprises N-(n-butyl)-1,2-benzisothiazolin-3-one and linoleamidopropyl PG-dimonium chloride phosphate. Preferably, a weight ratio of N-(n-butyl)-1,2-benzisothiazolin-3-one to linoleamidopropyl PG-dimonium chloride phosphate is from 1:8 to 1:500.

In one embodiment of the invention, the antimicrobial composition comprises N-(n-butyl)-1,2-benzisothiazolin-3-one and cocamidopropyl PG-dimonium chloride phosphate. Preferably, a weight ratio of N-(n-butyl)-1,2-benzisothiazolin-3-one to cocamidopropyl PG-dimonium chloride phosphate is from 1:0.1 to 1:400.

In one embodiment of the invention, the antimicrobial composition comprises N-(n-butyl)-1,2-benzisothiazolin-3-one and propylparaben. Preferably, a weight ratio of N-(n-butyl)-1,2-benzisothiazolin-3-one to propylparaben is from 1:1 to 1:500, more preferably from 1:4 to 1:400.

In one embodiment of the invention, the antimicrobial composition comprises N-(n-butyl)-1,2-benzisothiazolin-3-one and sorbic acid or its salts, preferably potassium sorbate. Preferably, a weight ratio of N-(n-butyl)-1,2-benzisothiazolin-3-one to sorbic acid or its salts is from 1:6 to 1:1200.

In one embodiment of the invention, the antimicrobial composition comprises N-(n-butyl)-1,2-benzisothiazolin-3-one and 1-(3-chloroallyl)-3,5,7-triaza-1-azoniaadamantane chloride. Preferably, a weight ratio of N-(n-butyl)-1,2-benzisothiazolin-3-one to 1-(3-chloroallyl)-3,5,7-triaza-1-azoniaadamantane chloride is from 1:0.5 to 1:200, more preferably from 1:1 to 1:200.

In one embodiment of the invention, the antimicrobial composition comprises N-(n-butyl)-1,2-benzisothiazolin-3-one and dehydroacetic acid or its salts, preferably sodium dehydroacetate. Preferably, a weight ratio of N-(n-butyl)-1,2-benzisothiazolin-3-one to dehydroacetic acid or its salts is from 1:0.5 to 1:7, more preferably from 1:0.7 to 1:5.

In one embodiment of the invention, the antimicrobial composition comprises N-(n-butyl)-1,2-benzisothiazolin-3-one and benzoic acid or its salts, preferably sodium benzoate. Preferably, a weight ratio of N-(n-butyl)-1,2-benzisothiazolin-3-one to benzoic acid or its salts is from 1:10 to 1:1600, more preferably from 1:13 to 1:1600.

In one embodiment of the invention, the antimicrobial composition comprises N-(n-butyl)-1,2-benzisothiazolin-3-one and citric acid or its salts, preferably sodium citrate. Preferably, a weight ratio of N-(n-butyl)-1,2-benzisothiazolin-3-one to citric acid or its salts is from 1:50 to 1:2400.

In one embodiment of the invention, the antimicrobial composition comprises N-methyl-1,2-benzisothiazolin-3-one and N-(n-butyl)-1,2-benzisothiazolin-3-one. Preferably, a weight ratio of N-methyl-1,2-benzisothiazolin-3-one to N-(n-butyl)-1,2-benzisothiazolin-3-one is from 1:0.1 to 1:30, more preferably from 1:0.5 to 1:24.

In one embodiment of the invention, the antimicrobial composition comprises N-methyl-1,2-benzisothiazolin-3-one and benzalkonium chloride. Preferably, a weight ratio of N-methyl-1,2-benzisothiazolin-3-one to benzalkonium chloride is from 1:0.1 to 1:20, more preferably from 1:0.2 to 1:20.

In one embodiment of the invention, the antimicrobial composition comprises N-methyl-1,2-benzisothiazolin-3-one and benzethonium chloride. Preferably, a weight ratio of N-methyl-1,2-benzisothiazolin-3-one to benzethonium chloride is from 1:0.3 to 1:0.6, more preferably from 1:0.4 to 1:0.6.

In one embodiment of the invention, the antimicrobial composition comprises N-methyl-1,2-benzisothiazolin-3-one and benzyl alcohol. Preferably, a weight ratio of N-methyl-1,2-benzisothiazolin-3-one to benzyl alcohol is from 1:1 to 1:800, more preferably from 1:5 to 1:800.

In one embodiment of the invention, the antimicrobial composition comprises N-methyl-1,2-benzisothiazolin-3-one and benzisothiazolinone. Preferably, a weight ratio of N-methyl-1,2-benzisothiazolin-3-one to benzisothiazolinone is from 1:0.1 to 1:25, more preferably from 1:0.3 to 1:20.

In one embodiment of the invention, the antimicrobial composition comprises N-methyl-1,2-benzisothiazolin-3-one and 2-bromo-2-nitropropane-1,3-diol. Preferably, a weight ratio of N-methyl-1,2-benzisothiazolin-3-one to 2-bromo-2-nitropropane-1,3-diol is from 1:0.1 to 1:100.

In one embodiment of the invention, the antimicrobial composition comprises N-methyl-1,2-benzisothiazolin-3-one and butylene glycol. Preferably, a weight ratio of N-methyl-1,2-benzisothiazolin-3-one to butylene glycol is from 1:5 to 1:400, more preferably from 1:13 to 1:375.

In one embodiment of the invention, the antimicrobial composition comprises N-methyl-1,2-benzisothiazolin-3-one and caprylyl glycol. Preferably, a weight ratio of N-methyl-1,2-benzisothiazolin-3-one to caprylyl glycol is from 1:25 to 1:1500.

In one embodiment of the invention, the antimicrobial composition comprises N-methyl-1,2-benzisothiazolin-3-one and chlorphenesin. Preferably, a weight ratio of N-methyl-1,2-benzisothiazolin-3-one to chlorphenesin is from 1:1 to 1:250, more preferably from 1:5 to 1:250.

In one embodiment of the invention, the antimicrobial composition comprises N-methyl-1,2-benzisothiazolin-3-one and dithio-2,2'-bis(N-methylbenzamide). Preferably, a weight ratio of N-methyl-1,2-benzisothiazolin-3-one to dithio-2,2'-bis(N-methylbenzamide) is from 1:0.1 to 1:100.

In one embodiment of the invention, the antimicrobial composition comprises N-methyl-1,2-benzisothiazolin-3-one and EDTA or its salts, preferably EDTA. Preferably, a weight ratio of N-methyl-1,2-benzisothiazolin-3-one to EDTA or its salts is from 1:1 to 1:400, more preferably from 1:10 to 1:320.

In one embodiment of the invention, the antimicrobial composition comprises N-methyl-1,2-benzisothiazolin-3-one and ethylparaben. Preferably, a weight ratio of N-methyl-1,2-benzisothiazolin-3-one to ethylparaben is from 1:5 to 1:500, more preferably from 1:7 to 1:400.

In one embodiment of the invention, the antimicrobial composition comprises N-methyl-1,2-benzisothiazolin-3-one and hexamidine diisethionate. Preferably, a weight ratio of N-methyl-1,2-benzisothiazolin-3-one to hexamidine diisethionate is from 1:0.1 to 1:5, more preferably from 1:0.1 to 1:3.

In one embodiment of the invention, the antimicrobial composition comprises N-methyl-1,2-benzisothiazolin-3-one and hexetidine. Preferably, a weight ratio of N-methyl-1,2-benzisothiazolin-3-one to hexetidine is from 1:0.1 to 1:40.

In one embodiment of the invention, the antimicrobial composition comprises N-methyl-1,2-benzisothiazolin-3-one and methylparaben. Preferably, a weight ratio of N-methyl-1,2-benzisothiazolin-3-one to methylparaben is from 1:1 to 1:400, more preferably from 1:2 to 1:400.

In one embodiment of the invention, the antimicrobial composition comprises N-methyl-1,2-benzisothiazolin-3-one and phenoxyethanol. Preferably, a weight ratio of -methyl-benzisothiazolinone to phenoxyethanol is from 1:120 to 1:160.

In one embodiment of the invention, the antimicrobial composition comprises N-methyl-1,2-benzisothiazolin-3-one and linoleamidopropyl PG-dimonium chloride phosphate. Preferably, a weight ratio of N-methyl-1,2-benzisothiazolin-3-one to linoleamidopropyl PG-dimonium chloride phosphate is from 1:3 to 1:400.

In one embodiment of the invention, the antimicrobial composition comprises N-methyl-1,2-benzisothiazolin-3-one and cocamidopropyl PG-dimonium chloride phosphate. Preferably, a weight ratio of N-methyl-1,2-benzisothiazolin-3-one to cocamidopropyl PG-dimonium chloride phosphate is from 1:0.1 to 1:125, and most preferably from 1:0.4 to 1:125.

In one embodiment of the invention, the antimicrobial composition comprises N-methyl-1,2-benzisothiazolin-3-one and sorbic acid or its salts, preferably potassium sorbate. Preferably, a weight ratio of N-methyl-1,2-benzisothiazolin-3-one to sorbic acid or its salts is from 1:5 to 1:600, more preferably from 1:8 to 1:600.

In one embodiment of the invention, the antimicrobial composition comprises N-methyl-1,2-benzisothiazolin-3-one and propylparaben. Preferably, a weight ratio of N-methyl-1,2-benzisothiazolin-3-one to propylparaben is from 1:10 to 1:1200, more preferably from 1:13 to 1:1200.

In one embodiment of the invention, the antimicrobial composition comprises N-methyl-1,2-benzisothiazolin-3-one and cis-1-(3-chloroallyl)-3,5,7-triaza-1-azoniaadamantane chloride. Preferably, a weight ratio of N-methyl-1,2-benzisothiazolin-3-one to cis-1-(3-chloroallyl)-3,5,7-triaza-1-azoniaadamantane chloride is from 1:0.2 to 1:400, more preferably from 1:0.3 to 1:200.

In one embodiment of the invention, the antimicrobial composition comprises N-methyl-1,2-benzisothiazolin-3-one and dehydroacetic acid or its salts, preferably sodium dehydroacetate. Preferably, a weight ratio of N-methyl-1,2-benzisothiazolin-3-one to dehydroacetic acid or its salts is from 1:1 to 1:5.

In one embodiment of the invention, the antimicrobial composition comprises N-methyl-1,2-benzisothiazolin-3-one and benzoic acid or its salts, preferably sodium benzoate. Preferably, a weight ratio of N-methyl-1,2-benzisothiazolin-3-one to benzoic acid or its salts is from 1:1 to 1:600, more preferably from 1:4 to 1:600.

In one embodiment of the invention, the antimicrobial composition comprises N-methyl-1,2-benzisothiazolin-3-one and citric acid or its salts, preferably sodium citrate. Preferably, a weight ratio of N-methyl-1,2-benzisothiazolin-3-one to citric acid or its salts is from 1:30 to 1:2500, more preferably from 1:33 to 1:2400.

In one embodiment of the invention, the antimicrobial composition comprises N-methyl-1,2-benzisothiazolin-3-one and zinc pyrithione. Preferably, a weight ratio of N-methyl-1,2-benzisothiazolin-3-one to zinc pyrithione is from 1:0.01 to 1:6, more preferably from 1:0.04 to 1:4.

The microbicides in the composition of this invention may be used "as is" or may first be formulated with a solvent or a solid carrier. Suitable solvents include, for example, water; glycols, such as ethylene glycol, propylene glycol, diethylene glycol, dipropylene glycol, polyethylene glycol, and polypropylene glycol; glycol ethers; alcohols, such as methanol, ethanol, propanol, phenethyl alcohol and phenoxypropanol; ketones, such as acetone and methyl ethyl ketone; esters, such as ethyl acetate, butyl acetate, triacetyl citrate, and glycerol triacetate; carbonates, such as propylene carbonate and dimethyl carbonate; and mixtures thereof. It is preferred that the solvent is selected from water, glycols, glycol ethers, esters and mixtures thereof. Suitable solid carriers include, for example, cyclodextrin, silicas, diatomaceous earth, waxes, cellulosic materials, alkali and alkaline earth (e.g., sodium, magnesium, potassium) metal salts (e.g., chloride, nitrate, bromide, sulfate) and charcoal.

When a microbicide component is formulated in a solvent, the formulation may optionally contain surfactants. When such formulations contain surfactants, they are generally in the form of emulsive concentrates, emulsions, microemulsive concentrates, or microemulsions. Emulsive concentrates form emulsions upon the addition of a sufficient amount of water. Microemulsive concentrates form microemulsions upon the addition of a sufficient amount of water. Such emulsive and microemulsive concentrates are generally well known in the art; it is preferred that such formulations are free of surfactants. U.S. Pat. No. 5,444,078 may be consulted for further general and specific details on the preparation of various microemulsions and microemulsive concentrates.

A microbicide component also can be formulated in the form of a dispersion. The solvent component of the dispersion can be an organic solvent or water, preferably water. Such dispersions can contain adjuvants, for example, co-solvents, thickeners, anti-freeze agents, dispersants, fillers, pigments, surfactants, biodispersants, sulfosuccinates, terpenes, furanones, polycations, stabilizers, scale inhibitors and anti-corrosion additives.

When both microbicides are each first formulated with a solvent, the solvent used for the first microbicide may be the same as or different from the solvent used to formulate the other commercial microbicide, although water is preferred for most industrial biocide applications. It is preferred that the two solvents are miscible.

Those skilled in the art will recognize that the microbicide components of the present invention may be added to a locus sequentially, simultaneously, or may be combined before being added to the locus. It is preferred that the first microbicide and the second microbicide component be added to a locus simultaneously or sequentially. When the microbicides are added simultaneously or sequentially, each may individual components may contain adjuvants, such as, for example, solvent, thickeners, anti-freeze agents, colorants, sequestrants (such as ethylenediamine-tetraacetic acid, ethylenediaminedisuccinic acid, iminodisuccinic acid and salts thereof), dispersants, surfactants, biodispersants, sulfosuccinates, terpenes, furanones, polycations, stabilizers, scale inhibitors and anti-corrosion additives.

The microbicidal compositions of the present invention can be used to inhibit the growth of microorganisms or higher forms of aquatic life (such as protozoans, invertebrates, bryozoans, dinoflagellates, crustaceans, mollusks, etc) by introducing a microbicidally effective amount of the compositions onto, into, or at a locus subject to microbial attack. Suitable loci include, for example: industrial process water; electrocoat deposition systems,; cooling towers; air washers; gas scrubbers; mineral slurries; wastewater treatment; ornamental fountains; reverse osmosis filtration; ultrafiltration; ballast water; evaporative condensers; heat exchangers; pulp and paper processing fluids and additives; starch; plastics; emulsions; dispersions; paints; latices; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids; household products, such as bathroom and kitchen cleaners; cosmetics; toiletries; shampoos; soaps; detergents; industrial cleaners; floor polishes; laundry rinse water; metalworking fluids; conveyor lubricants; hydraulic fluids; leather and leather products; textiles; textile products; wood and wood products, such as plywood, chipboard, wallboard, flakeboard, laminated beams, oriented strandboard, hardboard, and particleboard; petroleum processing fluids; fuel; oilfield fluids, such as injection water, fracture fluids, and drilling muds; agriculture adjuvant preservation; surfactant preservation; medical devices; diagnostic reagent preservation; food preservation, such as plastic or paper food wrap; food, beverage, and industrial process pasteurizers; toilet bowls; recreational water; pools; and spas.

Preferably, the microbicidal compositions of the present invention are used to inhibit the growth of microorganisms at a locus selected from one or more of mineral slurries, pulp and paper processing fluids and additives, starch, emulsions, dispersions, paints, latices, coatings, construction adhesives, such as ceramic adhesives, carpet backing adhesives, photographic chemicals, printing fluids, household products such as bathroom and kitchen cleaners, cosmetics, toiletries, shampoos, soaps, detergents, industrial cleaners, floor polishes, laundry rinse water, metal working fluids, textile products, agriculture adjuvant preservation, surfactant preservation, diagnostic reagent preservation, food preservation, and food, beverage, and industrial process pasteurizers.

The specific amount of the composition of this invention necessary to inhibit or control the growth of microorganisms and higher aquatic life forms in a locus depends upon the particular locus to be protected. Typically, the amount of the composition of the present invention to control the growth of microorganisms in a locus is sufficient if it provides from 0.1 to 1,000 ppm of the isothiazoline ingredient of the composition in the locus. It is preferred that the isothiazolone ingredients of the composition be present in the locus in an amount of at least 0.5 ppm, more preferably at least 4 ppm and most preferably at least 10 ppm. It is preferred that the isothiazolone ingredients of the composition be present in the locus in an amount of no more than 1000 ppm, more preferably no more than 500 ppm, and most preferably no more than 200 ppm.

In one embodiment of the invention, the composition is substantially free of enzymatic biocides. Preferably, when BBIT or MBIT and either methylparaben or ethylparaben are combined, the composition is substantially free of enzymatic biocides. Enzymatic biocides are enzymes having activity against microbes, as defined, e.g., in U.S. Pat. App. Pub. No. 2002/0028754.

EXAMPLES

Materials and Methods

The synergism of the combination of the present invention was demonstrated by testing a wide range of concentrations and ratios of the compounds.

One measure of synergism is the industrially accepted method described by Kull, F. C.; Eisman, P. C.; Sylwestrowicz, H. D. and Mayer, R. L., in *Applied Microbiology* 9:538-541 (1961), using the ratio determined by the formula:

$$Q_a/Q_A + Q_b/Q_B = \text{Synergy Index (``SI'')}$$

wherein:
$Q_A$=concentration of compound A (first component) in ppm, acting alone, which produced an end point (MIC of Compound A).
$Q_a$=concentration of compound A in ppm, in the mixture, which produced an end point.
$Q_B$=concentration of compound B (second component) in ppm, acting alone, which produced an end point (MIC of Compound B).
$Q_b$=concentration of compound B in ppm, in the mixture, which produced an end point.

When the sum of $Q_a/Q_A$ and $Q_b/Q_B$ is greater than one, antagonism is indicated. When the sum is equal to one, additivity is indicated, and when less than one, synergism is demonstrated. The lower the SI, the greater the synergy shown by that particular mixture. The minimum inhibitory concentration (MIC) of a microbicide is the lowest concentration tested under a specific set of conditions that prevents the growth of added microorganisms.

Synergy tests were conducted using standard microtiter plate assays with media designed for optimal growth of the test microorganism. Minimal salt medium supplemented with 0.2% glucose and 0.1% yeast extract (M9GY medium) was used for testing bacteria; Potato Dextrose Broth (PDB medium) was used for testing yeast and mold. In this method, a wide range of combinations of microbicides and other personal care raw materials was tested by conducting high resolution MIC assays in the presence of various concentrations of BBIT or MBIT. High resolution MICs were determined by adding varying amounts of microbicide to one column of a microtitre plate and doing subsequent ten-fold dilutions using an automated liquid handling system to obtain a series of endpoints ranging from 2 ppm to 10,000 ppm active ingredient.

The synergy of the combinations of the present invention was determined against a bacterium, Escherichia coli (E. coli—ATCC #8739), a yeast, Candida albicans (C. albicans—ATCC 10231), and a mold, Aspergillus niger (A. niger—ATCC 16404). The bacteria were used at a concentration of about $5 \times 10^6$ bacteria per mL and the yeast and mold at $5 \times 10^5$ fungi per mL. These microorganisms are representative of natural contaminants in many consumer and industrial applications. The plates were visually evaluated for microbial growth (turbidity) to determine the MIC after various incubation times at 25° C. (yeast and mold) or 30° C. (bacteria).

The test results for demonstration of synergy of the BBIT combinations of the present invention are shown below in Tables 1 through 26. In each test, First Component (A) was BBIT and the Second Component (B) was the other commercial microbicide. Each table shows the specific combinations of BBIT and the second component; results against the microorganisms tested with incubation times; the end-point activity in ppm measured by the MIC for BBIT alone ($Q_A$), for the second component alone ($Q_B$), for BBIT in the mixture ($Q_a$) and for second component in the mixture ($Q_b$); the calculated SI value; and the range of synergistic ratios for each combination tested (BBIT/second component or A/B).

The test results for demonstration of synergy of the MBIT combinations of the present invention are shown below in Tables 27 through 54. In each test, First Component (A) was MBIT and the Second Component (B) was the other commercial microbicide. Each table shows the specific combinations of MBIT and the second component; results against the microorganisms tested with incubation times; the end-point activity in ppm measured by the MIC for MBIT alone ($Q_A$), for the second component alone ($Q_B$), for MBIT in the mixture ($Q_a$) and for second component in the mixture ($Q_b$); the calculated SI value; and the range of synergistic ratios for each combination tested (MBIT/second component or A/B).

TABLE 1

First Component (A) = N-(n-butyl)-1,2-benzisothiazolinone (BBIT)
Second Component (B) = Benzalkonium chloride (Hyamine 3500)

| Microorganism | $Q_a$ | $Q_b$ | SI | A/B |
|---|---|---|---|---|
| E. coli 8739 - M9GY | 0 | 3 | 1.00 | — |
| (48 hours) | 16.667 | 40 | 1.00 | 1/2 |
| | 10 | 50 | 1.00 | 1/5 |
| | 12.5 | 60 | 1.00 | 1/5 |
| | 100 | 0 | 1.00 | — |
| C. albicans 10231 - PDB | 0 | 60 | 1.00 | — |
| (24 hours) | 2 | 4 | 0.40 | 1/2 |
| | 2 | 5 | 0.42 | 1/3 |
| | 2 | 6 | 0.43 | 1/3 |
| | 2 | 8 | 0.47 | 1/4 |
| | 2 | 10 | 0.50 | 1/5 |
| | 2 | 20 | 0.67 | 1/10 |
| | 2 | 30 | 0.83 | 1/15 |
| | 4 | 1 | 0.68 | 1/0.3 |
| | 4 | 2 | 0.70 | 1/0.5 |
| | 4 | 3 | 0.72 | 1/0.8 |
| | 4 | 4 | 0.73 | 1/1 |

TABLE 1-continued

First Component (A) = N-(n-butyl)-1,2-benzisothiazolinone (BBIT)
Second Component (B) = Benzalkonium chloride (Hyamine 3500)

| Microorganism | $Q_a$ | $Q_b$ | SI | A/B |
|---|---|---|---|---|
| | 4 | 5 | 0.75 | 1/1 |
| | 4 | 6 | 0.77 | 1/2 |
| | 4 | 8 | 0.80 | 1/2 |
| | 4 | 10 | 0.83 | 1/3 |
| | 7.5 | 0 | 1.00 | — |
| A. niger 16404 - PDB | 0 | 200 | 1.00 | — |
| (7 days) | 5 | 60 | 0.55 | 1/12 |
| | 5 | 80 | 0.65 | 1/16 |
| | 5 | 100 | 0.75 | 1/20 |
| | 10 | 50 | 0.75 | 1/5 |
| | 10 | 60 | 0.80 | 1/6 |
| | 10 | 80 | 0.90 | 1/8 |
| | 15 | 4 | 0.77 | 1/0.3 |
| | 15 | 5 | 0.78 | 1/0.3 |
| | 15 | 6 | 0.78 | 1/0.4 |
| | 15 | 8 | 0.79 | 1/0.5 |
| | 15 | 10 | 0.80 | 1/0.7 |
| | 15 | 20 | 0.85 | 1/1 |
| | 15 | 30 | 0.90 | 1/2 |
| | 20 | 0 | 1.00 | — |

The ratios of BBIT/benzalkonium chloride tested ranged from 1/0.02 to 1/500.

TABLE 2

First Component (A) = N-(n-butyl)-1,2-benzisothiazolinone (BBIT)
Second Component (B) = Benzethonium chloride (Hyamine 1622)

| Microorganism | $Q_a$ | $Q_b$ | SI | A/B |
|---|---|---|---|---|
| E. coli 8739 - M9GY | 0 | 20 | 1.00 | — |
| (72 hours) | 40 | 6 | 0.70 | 1/0.2 |
| | 40 | 8 | 0.80 | 1/0.2 |
| | 40 | 10 | 0.90 | 1/0.3 |
| | 50 | 3 | 0.65 | 1/0.06 |
| | 50 | 4 | 0.70 | 1/0.08 |
| | 50 | 5 | 0.75 | 1/0.1 |
| | 50 | 6 | 0.80 | 1/0.1 |
| | 50 | 8 | 0.90 | 1/0.2 |
| | 60 | 1 | 0.65 | 1/0.02 |
| | 60 | 2 | 0.70 | 1/0.03 |
| | 60 | 3 | 0.75 | 1/0.05 |
| | 60 | 4 | 0.80 | 1/0.07 |
| | 60 | 5 | 0.85 | 1/0.08 |
| | 60 | 6 | 0.90 | 1/0.1 |
| | 70 | 4 | 0.90 | 1/0.06 |
| | 100 | 0 | 1.00 | — |
| C. albicans 10231 - PDB | 0 | 4 | 1.00 | — |
| (24 hours) | 4 | 1 | 0.92 | 1/0.3 |
| | 6 | 0 | 1.00 | — |
| A. niger 16404 - PDB | 0 | 10 | 1.00 | — |
| (7 days) | 5 | 4 | 0.65 | 1/0.8 |
| | 5 | 5 | 0.75 | 1/0.8 |
| | 5 | 6 | 0.85 | 1/1 |
| | 10 | 4 | 0.90 | 1/0.4 |
| | 20 | 0 | 1.00 | — |

The ratios of BBIT/benzethonium chloride tested ranged from 1/0.02 to 1/500.

TABLE 3

First Component (A) = N-(n-butyl)-1,2-benzisothiazolinone (BBIT)
Second Component (B) = Benzyl alcohol

| Microorganism | $Q_a$ | $Q_b$ | SI | A/B |
|---|---|---|---|---|
| E. coli 8739 - M9GY | 0 | 2000 | 1.00 | — |
| (24 hours) | 100 | 2000 | 0.90 | 1/20 |
| | 200 | 0 | 1.00 | — |
| C. albicans 10231 - PDB | 0 | 3000 | 1.00 | — |
| (48 hours) | 2.5 | 600 | 0.45 | 1/240 |
| | 2.5 | 800 | 0.52 | 1/320 |

TABLE 3-continued

First Component (A) = N-(n-butyl)-1,2-benzisothiazolinone (BBIT)
Second Component (B) = Benzyl alcohol

| Microorganism | $Q_a$ | $Q_b$ | SI | A/B |
|---|---|---|---|---|
| | 2.5 | 1000 | 0.58 | 1/400 |
| | 2.5 | 2000 | 0.92 | 1/800 |
| | 5 | 400 | 0.63 | 1/80 |
| | 5 | 500 | 0.67 | 1/100 |
| | 5 | 600 | 0.70 | 1/120 |
| | 5 | 800 | 0.77 | 1/160 |
| | 5 | 1000 | 0.83 | 1/200 |
| | 7.5 | 20 | 0.76 | 1/3 |
| | 7.5 | 30 | 0.76 | 1/4 |
| | 7.5 | 40 | 0.76 | 1/5 |
| | 7.5 | 50 | 0.77 | 1/7 |
| | 7.5 | 60 | 0.77 | 1/8 |
| | 7.5 | 80 | 0.78 | 1/11 |
| | 7.5 | 100 | 0.78 | 1/13 |
| | 7.5 | 200 | 0.82 | 1/27 |
| | 7.5 | 300 | 0.85 | 1/40 |
| | 7.5 | 400 | 0.88 | 1/53 |
| | 7.5 | 500 | 0.92 | 1/67 |
| | 7.5 | 600 | 0.95 | 1/80 |
| | 10 | 0 | 1.00 | — |
| *A. niger* 16404 - PDB | 0 | 5000 | 1.00 | — |
| (3 days) | 5 | 5000 | 1.13 | 1/1000 |
| | 10 | 5000 | 1.25 | 1/500 |
| | 15 | 4000 | 1.18 | 1/267 |
| | 20 | 5000 | 1.50 | 1/250 |
| | 40 | 0 | 1.00 | — |

The ratios of BBIT/benzyl alcohol tested ranged from 1/0.2 to 1/5000.

TABLE 4

First Component (A) = N-(n-butyl)-1,2-benzisothiazolinone (BBIT)
Second Component (B) = Benzisothiazolinone (BIT)

| Microorganism | $Q_a$ | $Q_b$ | SI | A/B |
|---|---|---|---|---|
| *E. coli* 8739 - M9GY | 0 | 8 | 1.00 | — |
| (72 hours) | 40 | 1 | 0.53 | 1/0.03 |
| | 40 | 2 | 0.65 | 1/0.05 |
| | 40 | 3 | 0.78 | 1/0.08 |
| | 40 | 4 | 0.90 | 1/0.1 |
| | 50 | 1 | 0.63 | 1/0.02 |
| | 50 | 2 | 0.75 | 1/0.4 |
| | 50 | 3 | 0.88 | 1/0.06 |
| | 60 | 1 | 0.73 | 1/0.02 |
| | 60 | 2 | 0.85 | 1/0.03 |
| | 100 | 0 | 1.00 | — |
| *C. albicans* 10231 - PDB | 0 | 30 | 1.00 | — |
| (48 hours) | 2.5 | 8 | 0.60 | 1/3 |
| | 2.5 | 10 | 0.67 | 1/4 |
| | 5 | 3 | 0.77 | 1/0.6 |
| | 5 | 4 | 0.80 | 1/0.8 |
| | 5 | 5 | 0.83 | 1/1 |
| | 5 | 6 | 0.87 | 1/1.2 |
| | 5 | 8 | 0.93 | 1/1.6 |
| | 7.5 | 0 | 1.00 | — |
| *A. niger* 16404 - PDB | 0 | 100 | 1.00 | — |
| (7 days) | 5 | 80 | 0.86 | 1/16 |
| | 10 | 20 | 0.33 | 1/2 |
| | 10 | 30 | 0.43 | 1/3 |
| | 10 | 40 | 0.53 | 1/4 |
| | 10 | 50 | 0.63 | 1/5 |
| | 10 | 60 | 0.73 | 1/6 |
| | 10 | 80 | 0.93 | 1/8 |
| | 15 | 8 | 0.27 | 1/0.5 |
| | 15 | 10 | 0.29 | 1/0.7 |
| | 15 | 20 | 0.39 | 1/1 |
| | 15 | 30 | 0.49 | 1/2 |
| | 15 | 40 | 0.59 | 1/3 |
| | 15 | 50 | 0.69 | 1/3 |
| | 15 | 60 | 0.79 | 1/4 |
| | 20 | 10 | 0.35 | 1/0.5 |
| | 20 | 20 | 0.45 | 1/1 |
| | 20 | 30 | 0.55 | 1/2 |
| | 20 | 40 | 0.65 | 1/2 |
| | 20 | 50 | 0.75 | 1/3 |
| | 20 | 60 | 0.85 | 1/3 |
| | 40 | 2 | 0.52 | 1/0.05 |
| | 40 | 3 | 0.53 | 1/0.08 |
| | 40 | 4 | 0.54 | 1/0.1 |
| | 40 | 5 | 0.55 | 1/0.1 |
| | 40 | 6 | 0.56 | 1/0.1 |
| | 40 | 8 | 0.58 | 1/0.2 |
| | 40 | 10 | 0.60 | 1/0.3 |
| | 40 | 20 | 0.70 | 1/0.5 |
| | 40 | 30 | 0.80 | 1/0.8 |
| | 40 | 40 | 0.90 | 1/1 |
| | 80 | 0 | 1.00 | — |

The ratios of BBIT/benzisothiazolinone tested ranged from 1/0.02 to 1/500.

TABLE 5

First Component (A) = N-(n-butyl)-1,2-benzisothiazolinone (BBIT)
Second Component (B) = 2-bromo-2-nitro-propane-1,3-diol (BNPD)

| Microorganism | $Q_a$ | $Q_b$ | SI | A/B |
|---|---|---|---|---|
| *E. coli* 8739 - M9GY | 0 | 10 | 1.00 | — |
| (48 hours) | 40 | 1 | 0.50 | 1/0.03 |
| | 40 | 2 | 0.60 | 1/0.05 |
| | 40 | 3 | 0.70 | 1/0.08 |
| | 40 | 4 | 0.80 | 1/0.1 |
| | 40 | 5 | 0.90 | 1/0.1 |
| | 50 | 1 | 0.60 | 1/0.02 |
| | 50 | 2 | 0.70 | 1/0.04 |
| | 50 | 3 | 0.80 | 1/0.06 |
| | 50 | 4 | 0.90 | 1/0.08 |
| | 70 | 1 | 0.80 | 1/0.01 |
| | 70 | 2 | 0.90 | 1/0.03 |
| | 80 | 1 | 0.90 | 1/0.01 |
| | 100 | 0 | 1.00 | — |
| *C. albicans* 10231 - PDB | 0 | 2000 | 1.00 | — |
| (48 hours) | 2 | 1000 | 0.75 | 1/500 |
| | 4 | 20 | 0.51 | 1/5 |
| | 4 | 30 | 0.52 | 1/8 |
| | 4 | 40 | 0.52 | 1/10 |
| | 4 | 50 | 0.53 | 1/13 |
| | 4 | 60 | 0.53 | 1/15 |
| | 4 | 80 | 0.54 | 1/20 |
| | 4 | 100 | 0.55 | 1/25 |
| | 4 | 200 | 0.60 | 1/50 |
| | 4 | 300 | 0.65 | 1/75 |
| | 4 | 400 | 0.70 | 1/100 |
| | 4 | 500 | 0.75 | 1/125 |
| | 4 | 600 | 0.80 | 1/150 |
| | 4 | 800 | 0.90 | 1/200 |
| | 6 | 1 | 0.75 | 1/0.2 |
| | 6 | 2 | 0.75 | 1/0.3 |
| | 6 | 3 | 0.75 | 1/0.5 |
| | 6 | 4 | 0.75 | 1/0.7 |
| | 6 | 5 | 0.75 | 1/0.8 |
| | 6 | 6 | 0.75 | 1/1 |
| | 6 | 8 | 0.75 | 1/1 |
| | 6 | 10 | 0.76 | 1/2 |
| | 6 | 20 | 0.76 | 1/3 |
| | 6 | 30 | 0.77 | 1/5 |
| | 6 | 40 | 0.77 | 1/7 |
| | 6 | 50 | 0.78 | 1/8 |
| | 6 | 60 | 0.78 | 1/10 |
| | 6 | 80 | 0.79 | 1/13 |
| | 6 | 100 | 0.80 | 1/17 |
| | 6 | 200 | 0.85 | 1/33 |
| | 6 | 300 | 0.90 | 1/50 |
| | 8 | 0 | 1.00 | — |

TABLE 5-continued

First Component (A) = N-(n-butyl)-1,2-benzisothiazolinone (BBIT)
Second Component (B) = 2-bromo-2-nitro-propane-1,3-diol (BNPD)

| Microorganism | $Q_a$ | $Q_b$ | SI | A/B |
|---|---|---|---|---|
| A. niger 16404 - PDB | 0 | 2000 | 1.00 | — |
| (7 days) | 5 | 1000 | 0.75 | 1/200 |
| | 10 | 8 | 0.50 | 1/0.8 |
| | 10 | 10 | 0.51 | 1/1 |
| | 10 | 20 | 0.51 | 1/2 |
| | 10 | 30 | 0.52 | 1/3 |
| | 10 | 40 | 0.52 | 1/4 |
| | 10 | 50 | 0.53 | 1/5 |
| | 10 | 60 | 0.53 | 1/6 |
| | 10 | 80 | 0.54 | 1/8 |
| | 10 | 100 | 0.55 | 1/10 |
| | 10 | 200 | 0.60 | 1/20 |
| | 10 | 300 | 0.65 | 1/30 |
| | 10 | 400 | 0.70 | 1/40 |
| | 10 | 500 | 0.75 | 1/50 |
| | 10 | 600 | 0.80 | 1/60 |
| | 10 | 800 | 0.90 | 1/80 |
| | 20 | 0 | 1.00 | — |

The ratios of BBIT/2-bromo-2-nitro-propane-1,3-diol tested ranged from 1/0.01 to 1/500.

TABLE 6

First Component (A) = N-(n-butyl)-1,2-benzisothiazolinone (BBIT)
Second Component (B) = Butylene glycol

| Microorganism | $Q_a$ | $Q_b$ | SI | A/B |
|---|---|---|---|---|
| E. coli 8739 - M9GY | 0 | 20000 | 1.00 | — |
| (48 hours) | 40 | 5000 | 0.65 | 1/125 |
| | 40 | 6000 | 0.70 | 1/150 |
| | 40 | 8000 | 0.80 | 1/200 |
| | 40 | 10000 | 0.90 | 1/250 |
| | 50 | 2000 | 0.60 | 1/40 |
| | 50 | 3000 | 0.65 | 1/60 |
| | 50 | 4000 | 0.70 | 1/80 |
| | 50 | 5000 | 0.75 | 1/100 |
| | 50 | 6000 | 0.80 | 1/120 |
| | 50 | 8000 | 0.90 | 1/160 |
| | 70 | 2000 | 0.80 | 1/29 |
| | 70 | 3000 | 0.85 | 1/43 |
| | 70 | 4000 | 0.90 | 1/57 |
| | 80 | 200 | 0.81 | 1/3 |
| | 80 | 300 | 0.82 | 1/4 |
| | 80 | 400 | 0.82 | 1/5 |
| | 80 | 500 | 0.83 | 1/6 |
| | 80 | 600 | 0.83 | 1/8 |
| | 80 | 800 | 0.84 | 1/10 |
| | 80 | 1000 | 0.85 | 1/13 |
| | 80 | 2000 | 0.90 | 1/25 |
| | 100 | 0 | 1.00 | — |
| C. albicans 10231 - PDB | 0 | 20000 | 1.00 | — |
| (24 hours) | 2 | 10000 | 0.83 | 1/5000 |
| | 4 | 200 | 0.68 | 1/50 |
| | 4 | 300 | 0.68 | 1/75 |
| | 4 | 400 | 0.69 | 1/100 |
| | 4 | 500 | 0.69 | 1/125 |
| | 4 | 600 | 0.70 | 1/150 |
| | 4 | 800 | 0.71 | 1/200 |
| | 4 | 1000 | 0.72 | 1/250 |
| | 4 | 2000 | 0.77 | 1/500 |
| | 4 | 3000 | 0.82 | 1/750 |
| | 4 | 4000 | 0.87 | 1/1000 |
| | 4 | 5000 | 0.92 | 1/1250 |
| | 6 | 0 | 1.00 | — |
| A. niger 16404 - PDB | 0 | 10000 | 1.00 | — |
| (3 days) | 5 | 5000 | 0.83 | |
| | 5 | 6000 | 0.93 | |
| | 15 | 0 | 1.00 | |

The ratios of BBIT/butylene glycol tested ranged from 1/0.2 to 1/5000.

TABLE 7

First Component (A) = N-(n-butyl)-1,2-benzisothiazolinone (BBIT)
Second Component (B) = Caprylyl glycol

| Microorganism | $Q_a$ | $Q_b$ | SI | A/B |
|---|---|---|---|---|
| E. coli 8739 - M9GY | 0 | 2000 | 1.00 | — |
| (24 hours) | 40 | 400 | 0.60 | 1/10 |
| | 40 | 500 | 0.65 | 1/13 |
| | 40 | 600 | 0.70 | 1/15 |
| | 40 | 800 | 0.80 | 1/20 |
| | 40 | 1000 | 0.90 | 1/25 |
| | 50 | 200 | 0.60 | 1/4 |
| | 50 | 600 | 0.80 | 1/12 |
| | 50 | 800 | 0.90 | 1/16 |
| | 70 | 200 | 0.80 | 1/3 |
| | 70 | 300 | 0.85 | 1/4 |
| | 70 | 400 | 0.90 | 1/6 |
| | 80 | 200 | 0.90 | 1/3 |
| | 100 | 0 | 1.00 | — |
| C. albicans 10231 - PDB | 0 | 3000 | 1.00 | — |
| (24 hours) | 2 | 2000 | 0.92 | 1/1000 |
| | 4 | 500 | 0.67 | 1/125 |
| | 4 | 600 | 0.70 | 1/150 |
| | 4 | 800 | 0.77 | 1/200 |
| | 4 | 1000 | 0.83 | 1/250 |
| | 6 | 40 | 0.76 | 1/7 |
| | 6 | 50 | 0.77 | 1/8 |
| | 6 | 60 | 0.77 | 1/10 |
| | 6 | 80 | 0.78 | 1/13 |
| | 6 | 100 | 0.78 | 1/17 |
| | 6 | 200 | 0.82 | 1/33 |
| | 6 | 300 | 0.85 | 1/50 |
| | 6 | 400 | 0.88 | 1/67 |
| | 6 | 500 | 0.92 | 1/83 |
| | 8 | 0 | 1.00 | — |
| A. niger 16404 - PDB | 0 | 3000 | 1.00 | — |
| (7 days) | 5 | 1000 | 0.58 | 1/200 |
| | 5 | 2000 | 0.92 | 1/400 |
| | 10 | 1000 | 0.83 | 1/100 |
| | 20 | 0 | 1.00 | — |

The ratios of BBIT/caprylyl glycol tested ranged from 1/0.2 to 1/5000.

TABLE 8

First Component (A) = N-(n-butyl)-1,2-benzisothiazolinone (BBIT)
Second Component (B) = Chlorphenesin

| Microorganism | $Q_a$ | $Q_b$ | SI | A/B |
|---|---|---|---|---|
| E. coli 8739 - M9GY | 0 | 2000 | 1.00 | — |
| (24 hours) | 40 | 500 | 0.65 | 1/13 |
| | 40 | 600 | 0.70 | 1/115 |
| | 40 | 800 | 0.80 | 1/20 |
| | 40 | 1000 | 0.90 | 1/25 |
| | 50 | 300 | 0.65 | 1/6 |
| | 50 | 400 | 0.70 | 1/8 |
| | 50 | 500 | 0.75 | 1/10 |
| | 50 | 600 | 0.80 | 1/12 |
| | 50 | 800 | 0.90 | 1/16 |
| | 70 | 200 | 0.80 | 1/3 |
| | 70 | 300 | 0.85 | 1/4 |
| | 70 | 400 | 0.90 | 1/6 |
| | 80 | 100 | 0.85 | 1/1 |
| | 80 | 200 | 0.90 | 1/3 |
| | 100 | 0 | 1.00 | — |
| C. albicans 10231 - PDB | 0 | 2000 | 1.00 | — |
| (24 hours) | 2 | 800 | 0.65 | 1/400 |
| | 2 | 1000 | 0.75 | 1/500 |
| | 4 | 300 | 0.65 | 1/75 |
| | 4 | 400 | 0.70 | 1/100 |
| | 4 | 500 | 0.75 | 1/125 |
| | 4 | 600 | 0.80 | 1/150 |
| | 4 | 800 | 0.90 | 1/200 |
| | 6 | 10 | 0.76 | 1/2 |
| | 6 | 20 | 0.76 | 1/3 |
| | 6 | 30 | 0.77 | 1/5 |
| | 6 | 40 | 0.77 | 1/7 |

TABLE 8-continued

First Component (A) = N-(n-butyl)-1,2-benzisothiazolinone (BBIT)
Second Component (B) = Chlorphenesin

| Microorganism | $Q_a$ | $Q_b$ | SI | A/B |
|---|---|---|---|---|
| | 6 | 50 | 0.78 | 1/8 |
| | 6 | 60 | 0.78 | 1/10 |
| | 6 | 80 | 0.79 | 1/13 |
| | 6 | 100 | 0.80 | 1/17 |
| | 6 | 200 | 0.85 | 1/33 |
| | 6 | 300 | 0.90 | 1/50 |
| | 8 | 0 | 1.00 | — |
| A. niger 16404 - PDB (4 days) | 0 | 2000 | 1.00 | — |
| | 5 | 1000 | 0.83 | 1/200 |
| | 15 | 0 | 1.00 | — |

The ratios of BBIT/chlorphenesin tested ranged from 1/0.2 to 1/5000.

TABLE 9

First Component (A) = N-(n-butyl)-1,2-benzisothiazolinone (BBIT)
Second Component (B) = DMDM Hydantoin (DMDMH)

| Microorganism | $Q_a$ | $Q_b$ | SI | A/B |
|---|---|---|---|---|
| E. coli 8739 - M9GY (72 hours) | 0 | 200 | 1.00 | — |
| | 40 | 8 | 0.44 | 1/0.2 |
| | 40 | 10 | 0.45 | 1/0.3 |
| | 40 | 20 | 0.50 | 1/0.5 |
| | 40 | 30 | 0.55 | 1/0.8 |
| | 40 | 40 | 0.60 | 1/1 |
| | 40 | 50 | 0.65 | 1/1 |
| | 40 | 60 | 0.70 | 1/2 |
| | 40 | 80 | 0.80 | 1/2 |
| | 40 | 100 | 0.90 | 1/3 |
| | 50 | 3 | 0.52 | 1/0.06 |
| | 50 | 4 | 0.52 | 1/0.08 |
| | 50 | 5 | 0.53 | 1/0.1 |
| | 50 | 6 | 0.53 | 1/0.1 |
| | 50 | 8 | 0.54 | 1/0.2 |
| | 50 | 10 | 0.55 | 1/0.2 |
| | 50 | 20 | 0.60 | 1/0.4 |
| | 50 | 30 | 0.65 | 1/0.6 |
| | 50 | 40 | 0.70 | 1/0.8 |
| | 50 | 50 | 0.75 | 1/1 |
| | 50 | 60 | 0.80 | 1/1.2 |
| | 50 | 80 | 0.90 | 1/1.6 |
| | 60 | 6 | 0.63 | 1/0.1 |
| | 60 | 8 | 0.64 | 1/0.1 |
| | 60 | 10 | 0.65 | 1/0.2 |
| | 60 | 20 | 0.70 | 1/0.3 |
| | 60 | 30 | 0.75 | 1/0.5 |
| | 60 | 40 | 0.80 | 1/0.7 |
| | 60 | 50 | 0.85 | 1/0.8 |
| | 60 | 60 | 0.90 | 1/1 |
| | 80 | 8 | 0.84 | 1/0.1 |
| | 80 | 10 | 0.85 | 1/0.1 |
| | 80 | 20 | 0.90 | 1/0.3 |
| | 100 | 0 | 1.00 | — |
| C. albicans 10231 - PDB (24 hours) | 0 | 3000 | 1.00 | — |
| | 5 | 600 | 0.87 | 1/120 |
| | 5 | 800 | 0.93 | 1/160 |
| | 7.5 | 0 | 1.00 | — |
| A. niger 16404 - PDB (7 days) | 0 | 1000 | 1.00 | — |
| | 20 | 80 | 0.33 | 1/4 |
| | 20 | 100 | 0.35 | 1/5 |
| | 20 | 200 | 0.45 | 1/10 |
| | 20 | 300 | 0.55 | 1/15 |
| | 20 | 400 | 0.65 | 1/20 |
| | 20 | 500 | 0.75 | 1/25 |
| | 20 | 600 | 0.85 | 1/30 |
| | 40 | 100 | 0.60 | 1/3 |
| | 40 | 200 | 0.70 | 1/5 |
| | 40 | 300 | 0.80 | 1/8 |
| | 40 | 400 | 0.90 | 1/10 |
| | 80 | 0 | 1.00 | — |

The ratios of BBIT/DMDM Hydantoin tested ranged from 1/0.2 to 1/5000.

TABLE 10

First Component (A) = N-(n-butyl)-1,2-benzisothiazolinone (BBIT)
Second Component (B) = dithio-2,2'-bis(N-methylbenzamide) (DTBMA)

| Microorganism | $Q_a$ | $Q_b$ | SI | A/B |
|---|---|---|---|---|
| E. coli 8739 - M9GY (48 hours) | 0 | 60 | 1.00 | — |
| | 40 | 6 | 0.50 | 1/0.2 |
| | 40 | 8 | 0.53 | 1/0.2 |
| | 40 | 10 | 0.57 | 1/0.3 |
| | 40 | 20 | 0.73 | 1/0.5 |
| | 40 | 30 | 0.90 | 1/0.8 |
| | 50 | 3 | 0.55 | 1/1.06 |
| | 50 | 4 | 0.57 | 1/0.08 |
| | 50 | 5 | 0.58 | 1/0.1 |
| | 50 | 6 | 0.60 | 1/0.1 |
| | 50 | 8 | 0.63 | 1/1.2 |
| | 50 | 10 | 0.67 | 1/0.2 |
| | 50 | 20 | 0.83 | 1/0.4 |
| | 60 | 3 | 0.65 | 1/0.05 |
| | 60 | 4 | 0.67 | 1/0.07 |
| | 60 | 5 | 0.68 | 1/008 |
| | 60 | 6 | 0.70 | 1/0.1 |
| | 60 | 8 | 0.73 | 1/0.1 |
| | 60 | 10 | 0.77 | 1/0.2 |
| | 60 | 20 | 0.93 | 1/0.3 |
| | 70 | 3 | 0.75 | 1/0.04 |
| | 70 | 4 | 0.77 | 1/0.06 |
| | 70 | 5 | 0.78 | 1/0.07 |
| | 70 | 6 | 0.80 | 1/0.09 |
| | 70 | 7 | 0.82 | 1/0.1 |
| | 70 | 8 | 0.83 | 1/0.1 |
| | 70 | 10 | 0.87 | 1/0.1 |
| | 80 | 1 | 0.82 | 1/0.01 |
| | 80 | 2 | 0.83 | 1/0.03 |
| | 80 | 3 | 0.85 | 1/0.04 |
| | 80 | 4 | 0.87 | 1/0.05 |
| | 80 | 5 | 0.88 | 1/0.06 |
| | 80 | 6 | 0.90 | 1/0.08 |
| | 80 | 8 | 0.93 | 1/0.1 |
| | 100 | 0 | 1.00 | — |
| C. albicans 10231 - PDB (24 hours) | 0 | 2000 | 1.00 | — |
| | 8 | 40 | 0.55 | 1/5 |
| | 8 | 50 | 0.56 | 1/6 |
| | 8 | 60 | 0.56 | 1/8 |
| | 8 | 80 | 0.57 | 1/10 |
| | 8 | 100 | 0.58 | 1/13 |
| | 8 | 200 | 0.63 | 1/13 |
| | 8 | 300 | 0.68 | 1/38 |
| | 8 | 400 | 0.73 | 1/50 |
| | 8 | 500 | 0.78 | 1/63 |
| | 8 | 600 | 0.83 | 1/75 |
| | 8 | 800 | 0.93 | 1/100 |
| | 10 | 1 | 0.67 | 1/0.1 |
| | 10 | 2 | 0.67 | 1/0.2 |
| | 10 | 3 | 0.67 | 1/0.3 |
| | 10 | 4 | 0.67 | 1/0.4 |
| | 10 | 5 | 0.67 | 1/0.5 |
| | 10 | 6 | 0.67 | 1/0.6 |
| | 10 | 8 | 0.67 | 1/0.8 |
| | 10 | 10 | 0.67 | 1/1 |
| | 10 | 20 | 0.68 | 1/2 |
| | 10 | 30 | 0.68 | 1/3 |
| | 10 | 40 | 0.69 | 1/4 |
| | 10 | 50 | 0.69 | 1/5 |
| | 10 | 60 | 0.70 | 1/6 |
| | 10 | 80 | 0.71 | 1/8 |
| | 10 | 100 | 0.72 | 1/10 |
| | 10 | 200 | 0.77 | 1/20 |
| | 10 | 300 | 0.82 | 1/30 |
| | 10 | 400 | 0.87 | 1/40 |
| | 10 | 500 | 0.92 | 1/50 |
| | 15 | 0 | 1.00 | — |
| A. niger 16404 - PDB (7 days) | 0 | 1000 | 1.00 | — |
| | 5 | 800 | 0.93 | 1/160 |
| | 40 | 0 | 1.00 | — |

The ratios of BBIT/dithio-2,2'-bis(N-methylbenzamide) tested ranged from 1/0.02 to 1/500.

TABLE 11

First Component (A) = N-(n-butyl)-1,2-benzisothiazolinone (BBIT)
Second Component (B) = Ethylenediamine tetraacetic acid (EDTA)

| Microorganism | $Q_a$ | $Q_b$ | SI | A/B |
|---|---|---|---|---|
| E. coli 8739 - M9GY | 0 | 40000 | 1.00 | — |
| (72 hours) | 40 | 800 | 0.42 | 1/20 |
| | 40 | 1000 | 0.43 | 1/25 |
| | 40 | 1200 | 0.43 | 1/30 |
| | 40 | 1600 | 0.44 | 1/40 |
| | 40 | 2000 | 0.45 | 1/50 |
| | 40 | 4000 | 0.50 | 1/100 |
| | 40 | 6000 | 0.55 | 1/150 |
| | 40 | 8000 | 0.60 | 1/200 |
| | 40 | 10000 | 0.65 | 1/250 |
| | 40 | 12000 | 0.70 | 1/300 |
| | 40 | 16000 | 0.80 | 1/400 |
| | 40 | 20000 | 0.90 | 1/500 |
| | 50 | 400 | 0.51 | 1/8 |
| | 50 | 600 | 0.52 | 1/12 |
| | 50 | 800 | 0.52 | 1/16 |
| | 50 | 1000 | 0.53 | 1/20 |
| | 50 | 1200 | 0.53 | 1/24 |
| | 50 | 1600 | 0.54 | 1/32 |
| | 50 | 2000 | 0.55 | 1/40 |
| | 50 | 4000 | 0.60 | 1/80 |
| | 50 | 6000 | 0.65 | 1/120 |
| | 50 | 8000 | 0.70 | 1/160 |
| | 50 | 10000 | 0.75 | 1/200 |
| | 50 | 12000 | 0.80 | 1/240 |
| | 50 | 16000 | 0.90 | 1/320 |
| | 60 | 400 | 0.61 | 1/7 |
| | 60 | 600 | 0.62 | 1/10 |
| | 60 | 800 | 0.62 | 1/13 |
| | 60 | 1000 | 0.63 | 1/17 |
| | 60 | 1200 | 0.63 | 1/20 |
| | 60 | 1600 | 0.64 | 1/27 |
| | 60 | 2000 | 0.65 | 1/33 |
| | 60 | 4000 | 0.70 | 1/67 |
| | 60 | 6000 | 0.75 | 1/100 |
| | 60 | 8000 | 0.80 | 1/133 |
| | 60 | 10000 | 0.85 | 1/167 |
| | 60 | 12000 | 0.90 | 1/200 |
| | 70 | 200 | 0.71 | 1/3 |
| | 70 | 400 | 0.71 | 1/6 |
| | 70 | 600 | 0.72 | 1/9 |
| | 70 | 800 | 0.72 | 1/11 |
| | 70 | 1000 | 0.73 | 1/14 |
| | 70 | 1200 | 0.73 | 1/17 |
| | 70 | 1600 | 0.74 | 1/23 |
| | 70 | 2000 | 0.75 | 1/29 |
| | 70 | 4000 | 0.80 | 1/57 |
| | 70 | 6000 | 0.85 | 1/86 |
| | 70 | 8000 | 0.90 | 1/114 |
| | 70 | 10000 | 0.95 | 1/143 |
| | 80 | 400 | 0.81 | 1/5 |
| | 80 | 600 | 0.82 | 1/8 |
| | 80 | 800 | 0.82 | 1/40 |
| | 80 | 1000 | 0.83 | 1/13 |
| | 80 | 1200 | 0.83 | 1/15 |
| | 80 | 1600 | 0.84 | 1/20 |
| | 80 | 2000 | 0.85 | 1/25 |
| | 80 | 4000 | 0.90 | 1/50 |
| | 80 | 6000 | 0.95 | 1/75 |
| | 100 | 0 | 1.00 | — |
| C. albicans 10231 - PDB | 0 | 600 | 1.00 | — |
| (24 hours) | 2.5 | 60 | 0.43 | 1/24 |
| | 2.5 | 80 | 0.47 | 1/32 |
| | 2.5 | 100 | 0.50 | 1/40 |
| | 2.5 | 120 | 0.53 | 1/48 |
| | 2.5 | 160 | 0.60 | 1/64 |
| | 2.5 | 200 | 0.67 | 1/80 |
| | 5 | 60 | 0.77 | 1/12 |
| | 5 | 80 | 0.80 | 1/16 |
| | 5 | 100 | 0.83 | 1/20 |
| | 5 | 120 | 0.87 | 1/24 |
| | 5 | 160 | 0.93 | 1/32 |
| | 7.5 | 0 | 1.00 | — |
| A. niger 16404 - PDB | 0 | 1600 | 1.00 | — |
| (7 days) | 5 | 1000 | 0.75 | 1/200 |
| | 5 | 1200 | 0.88 | 1/240 |
| | 10 | 400 | 0.50 | 1/40 |
| | 10 | 600 | 0.63 | 1/60 |
| | 10 | 800 | 0.75 | 1/80 |
| | 10 | 1000 | 0.88 | 1/100 |
| | 15 | 400 | 0.63 | 1/27 |
| | 15 | 600 | 0.75 | 1/40 |
| | 15 | 800 | 0.88 | 1/53 |
| | 20 | 200 | 0.63 | 1/10 |
| | 20 | 400 | 0.75 | 1/20 |
| | 20 | 600 | 0.88 | 1/30 |
| | 40 | 0 | 1.00 | — |

The ratios of BBIT/ethylenediamine tetraacetic acid tested ranged from 1/0.4 to 1/10000.

TABLE 12

First Component (A) = N-(n-butyl)-1,2-benzisothiazolinone (BBIT)
Second Component (B) = Ethylparaben

| Microorganism | $Q_a$ | $Q_b$ | SI | A/B |
|---|---|---|---|---|
| E. coli 8739 - M9GY | 0 | 2000 | 1.00 | — |
| (24 hours) | 60 | 1000 | 0.80 | 1/17 |
| | 80 | 800 | 0.80 | 1/10 |
| | 80 | 1000 | 0.90 | 1/13 |
| | 100 | 200 | 0.60 | 1/2 |
| | 100 | 300 | 0.65 | 1/3 |
| | 100 | 400 | 0.70 | 1/4 |
| | 100 | 500 | 0.75 | 1/5 |
| | 100 | 600 | 0.80 | 1/6 |
| | 100 | 800 | 0.90 | 1/8 |
| | 200 | 0 | 1.00 | — |
| C. albicans 10231 - PDB | 0 | 800 | 1.00 | — |
| (24 hours) | 2.5 | 80 | 0.43 | 1/32 |
| | 2.5 | 100 | 0.46 | 1/40 |
| | 2.5 | 200 | 0.58 | 1/80 |
| | 2.5 | 300 | 0.71 | 1/120 |
| | 2.5 | 400 | 0.83 | 1/160 |
| | 2.5 | 500 | 0.96 | 1/200 |
| | 5 | 30 | 0.70 | 1/6 |
| | 5 | 40 | 0.72 | 1/8 |
| | 5 | 50 | 0.73 | 1/10 |
| | 5 | 60 | 0.74 | 1/12 |
| | 5 | 80 | 0.77 | 1/16 |
| | 5 | 100 | 0.79 | 1/20 |
| | 5 | 200 | 0.92 | 1/40 |
| | 7.5 | 0 | 1.00 | — |
| A. niger 16404 - PDB | 0 | 800 | 1.00 | — |
| (7 days) | 15 | 600 | 0.94 | 1/40 |
| | 80 | 0 | 1.00 | — |

The ratios of BBIT/ethylparaben tested ranged from 1/0.2 to 1/5000.

TABLE 13

First Component (A) = N-(n-butyl)-1,2-benzisothiazolinone (BBIT)
Second Component (B) = Hexamidine diisethionate

| Microorganism | $Q_a$ | $Q_b$ | SI | A/B |
|---|---|---|---|---|
| E. coli 8739 - M9GY | 0 | 100 | 1.00 | — |
| (48 hours) | 40 | 1 | 0.57 | 1/0.03 |
| | 40 | 2 | 0.73 | 1/0.05 |
| | 40 | 3 | 0.90 | 1/0.08 |
| | 50 | 1 | 0.67 | 1/0.02 |
| | 50 | 2 | 0.83 | 1/0.04 |
| | 60 | 1 | 0.77 | 1/0.02 |
| | 60 | 2 | 0.93 | 1/0.03 |
| | 70 | 1 | 0.87 | 1/0.01 |

TABLE 13-continued

First Component (A) = N-(n-butyl)-1,2-benzisothiazolinone (BBIT)
Second Component (B) = Hexamidine diisethionate

| Microorganism | $Q_a$ | $Q_b$ | SI | A/B |
|---|---|---|---|---|
| | 80 | 1 | 0.97 | 1/0.01 |
| | 6 | 0 | 1.00 | — |
| C. albicans 10231 - PDB | 0 | 10 | 1.00 | — |
| (24 hours) | 2 | 4 | 0.60 | 1/2 |
| | 2 | 5 | 0.70 | 1/2.5 |
| | 2 | 6 | 0.80 | 1/3 |
| | 4 | 2 | 0.60 | 1/0.5 |
| | 4 | 3 | 0.70 | 1/0.75 |
| | 4 | 4 | 0.80 | 1/1 |
| | 4 | 5 | 0.90 | 1/1.3 |
| | 6 | 1 | 0.70 | 1/0.2 |
| | 6 | 2 | 0.80 | 1/0.3 |
| | 6 | 3 | 0.90 | 1/0.5 |
| | 8 | 1 | 0.90 | 1/1.1 |
| | 10 | 0 | 1.00 | — |

The ratios of BBIT/hexamidine diisethionate tested ranged from 1/0.02 to 1/500.

TABLE 14

First Component (A) = N-(n-butyl)-1,2-benzisothiazolinone (BBIT)
Second Component (B) = Hexetidine

| Microorganism | $Q_a$ | $Q_b$ | SI | A/B |
|---|---|---|---|---|
| E. coli 8739 - M9GY | 0 | 200 | 1.00 | — |
| (72 hours) | 40 | 10 | 0.33 | 1/0.3 |
| | 40 | 20 | 0.45 | 1/1.5 |
| | 40 | 30 | 0.58 | 1/0.8 |
| | 40 | 40 | 0.70 | 1/1 |
| | 40 | 50 | 0.83 | 1/1.3 |
| | 40 | 60 | 0.95 | 1/1.5 |
| | 50 | 10 | 0.38 | 1/0.2 |
| | 50 | 20 | 0.50 | 1/0.4 |
| | 50 | 30 | 0.63 | 1/0.6 |
| | 50 | 40 | 0.75 | 1/0.8 |
| | 50 | 50 | 0.88 | 1/1 |
| | 60 | 4 | 0.35 | 1/0.07 |
| | 60 | 5 | 0.36 | 1/0.08 |
| | 60 | 6 | 0.38 | 1/0.1 |
| | 60 | 8 | 0.40 | 1/0.1 |
| | 60 | 10 | 0.43 | 1/0.2 |
| | 60 | 20 | 0.55 | 1/0.3 |
| | 60 | 30 | 0.68 | 1/0.5 |
| | 60 | 40 | 0.80 | 1/0.7 |
| | 60 | 50 | 0.93 | 1/0.8 |
| | 70 | 5 | 0.41 | 1/0.07 |
| | 70 | 6 | 0.43 | 1/0.09 |
| | 70 | 8 | 0.45 | 1/0.1 |
| | 70 | 10 | 0.48 | 1/0.1 |
| | 70 | 20 | 0.60 | 1/0.3 |
| | 70 | 30 | 0.73 | 1/0.4 |
| | 70 | 40 | 0.85 | 1/0.6 |
| | 70 | 50 | 0.98 | 1/0.7 |
| | 80 | 4 | 0.45 | 1/0.05 |
| | 80 | 5 | 0.46 | 1/0.06 |
| | 80 | 6 | 0.48 | 1/0.08 |
| | 80 | 8 | 0.50 | 1/0.1 |
| | 80 | 10 | 0.53 | 1/0.1 |
| | 80 | 20 | 0.65 | 1/0.3 |
| | 80 | 30 | 0.78 | 1/0.4 |
| | 80 | 40 | 0.90 | 1/0.5 |
| | 100 | 1 | 0.51 | 1/0.01 |
| | 100 | 2 | 0.53 | 1/0.02 |
| | 100 | 3 | 0.54 | 1/0.03 |
| | 100 | 4 | 0.55 | 1/0.04 |
| | 100 | 5 | 0.56 | 1/0.05 |
| | 100 | 6 | 0.58 | 1/0.06 |
| | 100 | 8 | 0.60 | 1/0.08 |
| | 100 | 10 | 0.63 | 1/0.1 |
| | 100 | 20 | 0.75 | 1/0.2 |
| | 100 | 30 | 0.88 | 1/0.3 |
| | 80 | 0 | 1.00 | — |
| C. albicans 10231 - PDB | 0 | 100 | 1.00 | — |
| (72 hours) | 2 | 40 | 0.53 | 1/20 |
| | 2 | 50 | 0.63 | 1/25 |
| | 2 | 60 | 0.73 | 1/30 |
| | 2 | 80 | 0.93 | 1/40 |
| | 4 | 30 | 0.57 | 1/8 |
| | 4 | 40 | 0.67 | 1/10 |
| | 4 | 50 | 0.77 | 1/13 |
| | 4 | 60 | 0.87 | 1/15 |
| | 6 | 20 | 0.60 | 1/3 |
| | 6 | 30 | 0.70 | 1/5 |
| | 6 | 40 | 0.80 | 1/7 |
| | 6 | 50 | 0.90 | 1/9 |
| | 8 | 5 | 0.58 | 1/0.6 |
| | 8 | 6 | 0.59 | 1/0.8 |
| | 8 | 8 | 0.61 | 1/1 |
| | 8 | 10 | 0.63 | 1/1 |
| | 8 | 20 | 0.73 | 1/3 |
| | 8 | 30 | 0.83 | 1/4 |
| | 8 | 40 | 0.93 | 1/5 |
| | 10 | 1 | 0.68 | 1/0.1 |
| | 10 | 2 | 0.69 | 1/0.2 |
| | 10 | 3 | 0.70 | 1/0.3 |
| | 10 | 4 | 0.71 | 1/0.4 |
| | 10 | 5 | 0.72 | 1/0.5 |
| | 10 | 6 | 0.73 | 1/0.6 |
| | 10 | 8 | 0.75 | 1/0.8 |
| | 10 | 10 | 0.77 | 1/1 |
| | 10 | 20 | 0.87 | 1/2 |
| | 10 | 30 | 0.97 | 1/3 |
| | 15 | 0 | 1.00 | — |
| A. niger 16404 - PDB | 0 | 100 | 1.00 | — |
| (4 days) | 5 | 50 | 0.75 | 1/10 |
| | 5 | 60 | 0.85 | 1/12 |
| | 10 | 40 | 0.90 | 1/4 |
| | 20 | 0 | 1.00 | — |

The ratios of BBIT/hexetidine tested ranged from 1/0.02 to 1/500.

TABLE 15

First Component (A) = N-(n-butyl)-1,2-benzisothiazolinone (BBIT)
Second Component (B) = Hexylene glycol

| Microorganism | $Q_a$ | $Q_b$ | SI | A/B |
|---|---|---|---|---|
| E. coli 8739 - M9GY | 0 | 20000 | 1.00 | — |
| (24 hours) | 40 | 20000 | 1.40 | 1/500 |
| | 50 | 20000 | 1.50 | 1/400 |
| | 60 | 20000 | 1.60 | 1/333 |
| | 80 | 20000 | 1.80 | 1/250 |
| | 100 | 0 | 1.00 | — |
| C. albicans 10231 - PDB | 0 | 20000 | 1.00 | — |
| (24 hours) | 2 | 20000 | 1.20 | 1/10000 |
| | 4 | 20000 | 1.40 | 1/5000 |
| | 6 | 20000 | 1.60 | 1/3333 |
| | 8 | 20000 | 1.80 | 1/2800 |
| | 10 | 0 | 1.00 | — |
| A. niger 16404 - PDB | 0 | 20000 | 1.00 | — |
| (3 days) | 5 | 20000 | 1.33 | 1/4000 |
| | 10 | 20000 | 1.67 | 1/2000 |
| | 15 | 0 | 1.00 | — |

The ratios of BBIT/hexylene glycol tested ranged from 1/0.2 to 1/5000. No synergy was observed between BBIT and hexylene glycol.

TABLE 16

First Component (A) = N-(n-butyl)-1,2-benzisothiazolinone (BBIT)
Second Component (B) = Methylparaben

| Microorganism | $Q_a$ | $Q_b$ | SI | A/B |
|---|---|---|---|---|
| E. coli 8739 - M9GY | 0 | 2000 | 1.00 | — |
| (72 hours) | 40 | 400 | 0.60 | 1/10 |
|  | 40 | 500 | 0.65 | 1/13 |
|  | 40 | 600 | 0.70 | 1/15 |
|  | 40 | 800 | 0.80 | 1/20 |
|  | 40 | 1000 | 0.90 | 1/25 |
|  | 50 | 100 | 0.55 | 1/2 |
|  | 50 | 200 | 0.60 | 1/4 |
|  | 50 | 300 | 0.65 | 1/6 |
|  | 50 | 400 | 0.70 | 1/8 |
|  | 50 | 500 | 0.75 | 1/10 |
|  | 50 | 600 | 0.80 | 1/12 |
|  | 50 | 800 | 0.90 | 1/16 |
|  | 60 | 30 | 0.62 | 1/0.5 |
|  | 60 | 40 | 0.62 | 1/0.7 |
|  | 60 | 50 | 0.63 | 1/0.8 |
|  | 60 | 60 | 0.63 | 1/1 |
|  | 60 | 80 | 0.64 | 1/1 |
|  | 60 | 100 | 0.65 | 1/2 |
|  | 60 | 200 | 0.70 | 1/3 |
|  | 60 | 300 | 0.75 | 1/5 |
|  | 60 | 400 | 0.80 | 1/7 |
|  | 60 | 500 | 0.85 | 1/8 |
|  | 60 | 600 | 0.90 | 1/10 |
|  | 70 | 300 | 0.85 | 1/4 |
|  | 70 | 400 | 0.90 | 1/6 |
|  | 70 | 500 | 0.95 | 1/7 |
|  | 80 | 300 | 0.95 | 1/4 |
|  | 100 | 0 | 1.00 | — |
| C. albicans 10231 - PDB | 0 | 1000 | 1.00 | — |
| (24 hours) | 2.5 | 100 | 0.43 | 1/40 |
|  | 2.5 | 200 | 0.53 | 1/80 |
|  | 2.5 | 300 | 0.63 | 1/120 |
|  | 2.5 | 400 | 0.73 | 1/160 |
|  | 2.5 | 500 | 0.83 | 1/200 |
|  | 2.5 | 600 | 0.93 | 1/240 |
|  | 5 | 40 | 0.71 | 1/8 |
|  | 5 | 50 | 0.72 | 1/10 |
|  | 5 | 60 | 0.73 | 1/12 |
|  | 5 | 80 | 0.75 | 1/16 |
|  | 5 | 100 | 0.77 | 1/20 |
|  | 5 | 200 | 0.87 | 1/40 |
|  | 5 | 300 | 0.97 | 1/60 |
|  | 7.5 | 0 | 1.00 | — |
| A. niger 16404 - PDB | 0 | 1000 | 1.00 | — |
| (3 days) | 5 | 600 | 0.73 | 1/120 |
|  | 5 | 800 | 0.93 | 1/160 |
|  | 40 | 0 | 1.00 | — |

The ratios of BBIT/methylparaben tested ranged from 1/0.2 to 1/5000.

TABLE 17

First Component (A) = N-(n-butyl)-1,2-benzisothiazolinone (BBIT)
Second Component (B) = Pentylene glycol

| Microorganism | $Q_a$ | $Q_b$ | SI | A/B |
|---|---|---|---|---|
| E. coli 8739 - M9GY | 0 | 20000 | 1.00 | — |
| (24 hours) | 40 | 20000 | 1.40 | 1/500 |
|  | 60 | 20000 | 1.60 | 1/333 |
|  | 80 | 20000 | 1.80 | 1/250 |
|  | 100 | 0 | 1.00 | — |
| C. albicans 10231 - PDB | 0 | 20000 | 1.00 | — |
| (24 hours) | 2 | 20000 | 1.02 | 1/10000 |
|  | 4 | 20000 | 1.04 | 1/5000 |
|  | 8 | 20000 | 1.08 |  |
|  | 10 | 20000 | 1.10 |  |
|  | 15 | 0 | 1.00 | — |

TABLE 17-continued

First Component (A) = N-(n-butyl)-1,2-benzisothiazolinone (BBIT)
Second Component (B) = Pentylene glycol

| Microorganism | $Q_a$ | $Q_b$ | SI | A/B |
|---|---|---|---|---|
| A. niger 16404 - PDB | 0 | 20000 | 1.00 | — |
| (4 days) | 5 | 20000 | 1.05 |  |
|  | 10 | 20000 | 1.10 |  |
|  | 15 | 20000 | 1.15 |  |
|  | 20 | 0 | 1.00 | — |

The ratios of BBIT/pentylene glycol tested ranged from 1/0.2 to 1/5000. No synergy was observed between BBIT and pentylene glycol.

TABLE 18

First Component (A) = N-(n-butyl)-1,2-benzisothiazolinone (BBIT)
Second Component (B) = Phenoxyethanol

| Microorganism | $Q_a$ | $Q_b$ | SI | A/B |
|---|---|---|---|---|
| E. coli 8739 - M9GY | 0 | 5000 | 1.00 | — |
| (72 hours) | 50 | 800 | 0.66 | 1/16 |
|  | 50 | 1000 | 0.70 | 1/20 |
|  | 50 | 2000 | 0.90 | 1/40 |
|  | 60 | 60 | 0.61 | 1/1 |
|  | 60 | 80 | 0.62 | 1/1 |
|  | 60 | 100 | 0.62 | 1/2 |
|  | 60 | 200 | 0.64 | 1/3 |
|  | 60 | 300 | 0.66 | 1/5 |
|  | 60 | 400 | 0.68 | 1/7 |
|  | 60 | 500 | 0.70 | 1/8 |
|  | 60 | 600 | 0.72 | 1/10 |
|  | 60 | 800 | 0.76 | 1/13 |
|  | 60 | 1000 | 0.80 | 1/17 |
|  | 70 | 1000 | 0.90 | 1/14 |
|  | 100 | 0 | 1.00 | — |
| C. albicans 10231 - PDB | 0 | 4000 | 1.00 | — |
| (24 hours) | 2.5 | 1000 | 0.58 | 1/400 |
|  | 2.5 | 2000 | 0.83 | 1/800 |
|  | 5 | 500 | 0.79 | 1/100 |
|  | 5 | 600 | 0.82 | 1/120 |
|  | 5 | 800 | 0.87 | 1/160 |
|  | 5 | 1000 | 0.92 | 1/200 |
|  | 7.5 | 0 | 1.00 | — |
| A. niger 16404 - PDB | 0 | 4000 | 1.00 | — |
| (7 days) | 5 | 3000 | 0.88 | 1/600 |
|  | 40 | 0 | 1.00 | — |

The ratios of BBIT/phenoxyethanol tested ranged from 1/0.2 to 1/5000.

TABLE 19

First Component (A) = N-(n-butyl)-1,2-benzisothiazolinone (BBIT)
Second Component (B) = linoleamidopropyl PG-dimonium chloride phosphate (Phospholipid EFA)

| Microorganism | $Q_a$ | $Q_b$ | SI | A/B |
|---|---|---|---|---|
| E. coli 8739 - M9GY | 0 | 600 | 1.00 | — |
| (48 hours) | 40 | 400 | 0.87 | 1/10 |
|  | 50 | 400 | 0.92 | 1/8 |
|  | 200 | 0 | 1.00 | — |
| C. albicans 10231 - PDB | 0 | 2000 | 1.00 | — |
| (24 hours) | 2 | 800 | 0.60 | 1/400 |
|  | 2 | 1000 | 0.70 | 1/500 |
|  | 4 | 600 | 0.70 | 1/150 |
|  | 4 | 800 | 0.80 | 1/200 |
|  | 4 | 1000 | 0.90 | 1/250 |
|  | 6 | 500 | 0.85 | 1/83 |
|  | 6 | 600 | 0.90 | 1/100 |
|  | 10 | 0 | 1.00 | — |
| A. niger 16404 - PDB | 0 | 2000 | 1.00 | — |
| (4 days) | 5 | 600 | 0.55 | 1/120 |
|  | 5 | 800 | 0.65 | 1/160 |
|  | 5 | 1000 | 0.75 | 1/200 |

TABLE 19-continued

First Component (A) = N-(n-butyl)-1,2-benzisothiazolinone (BBIT)
Second Component (B) = linoleamidopropyl PG-dimonium
chloride phosphate (Phospholipid EFA)

| Microorganism | $Q_a$ | $Q_b$ | SI | A/B |
|---|---|---|---|---|
| | 10 | 600 | 0.80 | 1/60 |
| | 10 | 800 | 0.90 | 1/80 |
| | 20 | 0 | 1.00 | — |

The ratios of BBIT/linoleamidopropyl PG-dimonium chloride phosphate tested ranged from 1/0.02 to 1/500.

TABLE 20

First Component (A) = N-(n-butyl)-1,2-benzisothiazolinone (BBIT)
Second Component (B) = cocamidopropyl PG-dimonium
chloride phosphate (Phospholipid PTC)

| Microorganism | $Q_a$ | $Q_b$ | SI | A/B |
|---|---|---|---|---|
| E. coli 8739 - M9GY (72 hours) | 0 | 80 | 1.00 | — |
| | 40 | 20 | 0.45 | 1/0.5 |
| | 40 | 30 | 0.58 | 1/0.75 |
| | 40 | 40 | 0.70 | 1/1 |
| | 40 | 50 | 0.83 | 1/0.3 |
| | 40 | 60 | 0.95 | 1/2 |
| | 50 | 20 | 0.50 | 1/0.4 |
| | 50 | 30 | 0.63 | 1/0.6 |
| | 50 | 40 | 0.75 | 1/0.8 |
| | 50 | 50 | 0.88 | 1/1 |
| | 60 | 8 | 0.40 | 1/0.1 |
| | 60 | 10 | 0.43 | 1/0.2 |
| | 60 | 20 | 0.55 | 1/0.3 |
| | 60 | 30 | 0.68 | 1/0.5 |
| | 60 | 40 | 0.80 | 1/0.7 |
| | 60 | 50 | 0.93 | 1/0.8 |
| | 70 | 10 | 0.48 | 1/0.1 |
| | 70 | 20 | 0.60 | 1/0.3 |
| | 70 | 30 | 0.73 | 1/0.4 |
| | 70 | 40 | 0.85 | 1/0.6 |
| | 70 | 50 | 0.98 | 1/0.7 |
| | 80 | 10 | 0.53 | 1/0.1 |
| | 80 | 20 | 0.65 | 1/0.3 |
| | 80 | 30 | 0.78 | 1/0.4 |
| | 80 | 40 | 0.90 | 1/0.5 |
| | 100 | 3 | 0.54 | 1/0.3 |
| | 100 | 4 | 0.55 | 1/0.4 |
| | 100 | 5 | 0.56 | 1/0.5 |
| | 100 | 6 | 0.58 | 1/0.6 |
| | 100 | 8 | 0.60 | 1/0.8 |
| | 100 | 10 | 0.63 | 1/0.1 |
| | 100 | 20 | 0.75 | 1/0.2 |
| | 100 | 30 | 0.88 | 1/0.3 |
| | 200 | 0 | 1.00 | — |
| C. albicans 10231 - PDB (24 hours) | 0 | 1000 | 1.00 | — |
| | 2 | 600 | 0.73 | 1/300 |
| | 2 | 800 | 0.93 | 1/400 |
| | 4 | 400 | 0.67 | 1/400 |
| | 4 | 500 | 0.77 | 1/125 |
| | 4 | 600 | 0.87 | 1/150 |
| | 6 | 300 | 0.70 | 1/50 |
| | 6 | 400 | 0.80 | 1/67 |
| | 6 | 500 | 0.90 | 1/83 |
| | 8 | 4 | 0.54 | 1/0.5 |
| | 8 | 5 | 0.54 | 1/0.6 |
| | 8 | 6 | 0.54 | 1/0.8 |
| | 8 | 8 | 0.54 | 1/1 |
| | 8 | 10 | 0.54 | 1/1 |
| | 8 | 20 | 0.55 | 1/6 |
| | 8 | 30 | 0.56 | 1/4 |
| | 8 | 40 | 0.57 | 1/5 |
| | 8 | 50 | 0.58 | 1/6 |
| | 8 | 60 | 0.59 | 1/8 |
| | 8 | 80 | 0.61 | 1/10 |
| | 8 | 100 | 0.63 | 1/13 |
| | 8 | 200 | 0.73 | 1/25 |
| | 8 | 300 | 0.83 | 1/38 |
| | 8 | 400 | 0.93 | 1/50 |

TABLE 20-continued

First Component (A) = N-(n-butyl)-1,2-benzisothiazolinone (BBIT)
Second Component (B) = cocamidopropyl PG-dimonium
chloride phosphate (Phospholipid PTC)

| Microorganism | $Q_a$ | $Q_b$ | SI | A/B |
|---|---|---|---|---|
| | 10 | 3 | 0.67 | 1/0.3 |
| | 10 | 4 | 0.67 | 1/0.4 |
| | 10 | 5 | 0.67 | 1/0.5 |
| | 10 | 6 | 0.67 | 1/0.6 |
| | 10 | 8 | 0.67 | 1/0.8 |
| | 10 | 10 | 0.68 | 1/1 |
| | 10 | 20 | 0.69 | 1/2 |
| | 10 | 30 | 0.70 | 1/3 |
| | 10 | 40 | 0.71 | 1/4 |
| | 10 | 50 | 0.72 | 1/5 |
| | 10 | 60 | 0.73 | 1/6 |
| | 10 | 80 | 0.75 | 1/8 |
| | 10 | 100 | 0.77 | 1/10 |
| | 10 | 200 | 0.87 | 1/20 |
| | 10 | 300 | 0.97 | 1/30 |
| | 15 | 0 | 1.00 | — |
| A. niger 16404 - PDB (3 days) | 0 | 1000 | 1.00 | — |
| | 5 | 500 | 0.83 | 1/100 |
| | 5 | 600 | 0.93 | 1/120 |
| | 10 | 200 | 0.87 | 1/20 |
| | 10 | 300 | 0.97 | 1/30 |
| | 15 | 0 | 1.00 | — |

The ratios of BBIT/cocamidopropyl PG-dimonium chloride phosphate tested ranged from 1/0.02 to 1/500.

TABLE 21

First Component (A) = N-(n-butyl)-1,2-benzisothiazolinone (BBIT)
Second Component (B) = Potassium sorbate

| Microorganism | $Q_a$ | $Q_b$ | SI | A/B |
|---|---|---|---|---|
| E. coli 8739 - M9GY (24 hours) | 0 | 20000 | 1.00 | — |
| | 20 | 20000 | 1.10 | 1/1000 |
| | 40 | 20000 | 1.20 | 1/500 |
| | 60 | 20000 | 1.30 | 1/333 |
| | 80 | 20000 | 1.40 | 1/250 |
| | 100 | 20000 | 1.50 | 1/200 |
| | 200 | 0 | 1.00 | — |
| C. albicans 10231 - PDB (24 hours) | 0 | 400 | 1.00 | — |
| | 2.5 | 100 | 0.58 | 1/40 |
| | 2.5 | 200 | 0.83 | 1/80 |
| | 5 | 30 | 0.74 | 1/6 |
| | 5 | 60 | 0.82 | 1/12 |
| | 5 | 80 | 0.87 | 1/16 |
| | 5 | 100 | 0.92 | 1/20 |
| | 7.5 | 0 | 1.00 | — |
| A. niger 16404 - PDB (3 days) | 0 | 8000 | 1.00 | — |
| | 5 | 6000 | 0.88 | 1/1200 |
| | 10 | 4000 | 0.75 | 1/400 |
| | 10 | 5000 | 0.88 | 1/500 |
| | 15 | 4000 | 0.88 | 1/267 |
| | 20 | 600 | 0.58 | 1/30 |
| | 20 | 800 | 0.60 | 1/40 |
| | 20 | 1000 | 0.63 | 1/50 |
| | 20 | 2000 | 0.75 | 1/100 |
| | 20 | 3000 | 0.88 | 1/150 |
| | 40 | 0 | 1.00 | — |

The ratios of BBIT/potassium sorbate tested ranged from 1/0.2 to 1/5000.

TABLE 22

First Component (A) = N-(n-butyl)-1,2-benzisothiazolinone (BBIT)
Second Component (B) = Propylparaben

| Microorganism | $Q_a$ | $Q_b$ | SI | A/B |
|---|---|---|---|---|
| E. coli 8739 - M9GY (24 hours) | 0 | 2000 | 1.00 | — |
| | 20 | 2000 | 1.10 | 1/100 |
| | 40 | 2000 | 1.20 | 1/50 |

TABLE 22-continued

First Component (A) = N-(n-butyl)-1,2-benzisothiazolinone (BBIT)
Second Component (B) = Propylparaben

| Microorganism | $Q_a$ | $Q_b$ | SI | A/B |
|---|---|---|---|---|
|  | 60 | 2000 | 1.30 | 1/33 |
|  | 80 | 2000 | 1.40 | 1/25 |
|  | 100 | 2000 | 1.50 | 1/25 |
|  | 200 | 0 | 1.00 | — |
| C. albicans 10231 - PDB | 0 | 2000 | 1.00 | — |
| (24 hours) | 2.5 | 30 | 0.35 | 1/12 |
|  | 2.5 | 40 | 0.35 | 1/16 |
|  | 2.5 | 50 | 0.36 | 1/20 |
|  | 2.5 | 60 | 0.36 | 1/24 |
|  | 2.5 | 80 | 0.37 | 1/32 |
|  | 2.5 | 100 | 0.38 | 1/40 |
|  | 2.5 | 200 | 0.43 | 1/80 |
|  | 2.5 | 300 | 0.48 | 1/120 |
|  | 2.5 | 400 | 0.53 | 1/160 |
|  | 2.5 | 500 | 0.58 | 1/200 |
|  | 2.5 | 600 | 0.63 | 1/240 |
|  | 2.5 | 800 | 0.73 | 1/320 |
|  | 2.5 | 1000 | 0.83 | 1/400 |
|  | 5 | 20 | 0.68 | 1/4 |
|  | 5 | 30 | 0.68 | 1/6 |
|  | 5 | 40 | 0.69 | 1/8 |
|  | 5 | 50 | 0.69 | 1/10 |
|  | 5 | 60 | 0.70 | 1/12 |
|  | 5 | 80 | 0.71 | 1/16 |
|  | 5 | 100 | 0.72 | 1/20 |
|  | 5 | 200 | 0.77 | 1/40 |
|  | 5 | 300 | 0.82 | 1/60 |
|  | 5 | 400 | 0.87 | 1/80 |
|  | 5 | 500 | 0.92 | 1/100 |
|  | 5 | 600 | 0.97 | 1/120 |
|  | 7.5 | 0 | 1.00 | — |
| A. niger 16404 - PDB | 0 | 2000 | 1.00 | — |
| (7 days) | 10 | 1000 | 0.63 | 1/100 |
|  | 20 | 800 | 0.65 | 1/40 |
|  | 20 | 1000 | 0.75 | 1/80 |
|  | 40 | 800 | 0.90 | 1/20 |
|  | 80 | 0 | 1.00 | — |

The ratios of BBIT/propylparaben tested ranged from 1/0.2 to 1/5000.

TABLE 23

First Component (A) = N-(n-butyl)-1,2-benzisothiazolinone (BBIT)
Second Component (B) = Quaternium-15 (active-1-(3-chloroallyl)-3,5,7-triaza-1-azoniaadamantane chloride)

| Microorganism | $Q_a$ | $Q_b$ | SI | A/B |
|---|---|---|---|---|
| E. coli 8739 - M9GY | 0 | 200 | 1.00 | — |
| (72 hours) | 40 | 50 | 0.43 | 1/1 |
|  | 40 | 60 | 0.43 | 1/1 |
|  | 40 | 80 | 0.44 | 1/2 |
|  | 40 | 100 | 0.45 | 1/3 |
|  | 40 | 200 | 0.50 | 1/5 |
|  | 40 | 300 | 0.55 | 1/8 |
|  | 40 | 400 | 0.60 | 1/10 |
|  | 40 | 500 | 0.65 | 1/13 |
|  | 40 | 600 | 0.70 | 1/15 |
|  | 40 | 800 | 0.80 | 1/20 |
|  | 200 | 0 | 1.00 | — |
| C. albicans 10231 - PDB | 0 | 600 | 1.00 | — |
| (24 hours) | 5 | 50 | 0.75 | 1/10 |
|  | 5 | 60 | 0.77 | 1/12 |
|  | 5 | 80 | 0.80 | 1/16 |
|  | 5 | 100 | 0.83 | 1/20 |
|  | 7.5 | 0 | 1.00 | — |
| A. niger 16404 - PDB | 0 | 3000 | 1.00 | — |
| (4 days) | 10 | 1000 | 0.58 | 1/100 |
|  | 10 | 2000 | 0.92 | 1/200 |
|  | 20 | 1000 | 0.83 | 1/50 |
|  | 40 | 0 | 1.00 | — |

The ratios of BBIT/1-(3-chloroallyl)-3,5,7-triaza-1-azoniaadamantane chloride tested ranged from 1/0.02 to 1/5000.

TABLE 24

First Component (A) = N-(n-butyl)-1,2-benzisothiazolinone (BBIT)
Second Component (B) = dehydroacetic acid, sodium salt (SDHA)

| Microorganism | $Q_a$ | $Q_b$ | SI | A/B |
|---|---|---|---|---|
| E. coli 8739 - M9GY | 0 | 20000 | 1.00 | — |
| (24 hours) | 20 | 20000 | 1.10 | 1/1000 |
|  | 40 | 20000 | 1.20 | 1/500 |
|  | 60 | 20000 | 1.30 | 1/333 |
|  | 80 | 20000 | 1.40 | 1/250 |
|  | 100 | 20000 | 1.50 | 1/200 |
|  | 200 | 0 | 1.00 | — |
| C. albicans 10231 - PDB | 0 | 40 | 1.00 | — |
| (24 hours) | 4 | 10 | 0.75 | 1/3 |
|  | 6 | 4 | 0.85 | 1/0.7 |
|  | 6 | 5 | 0.88 | 1/0.8 |
|  | 6 | 6 | 0.90 | 1/1 |
|  | 6 | 8 | 0.95 | 1/1 |
|  | 8 | 0 | 1.00 | — |
| A. niger 16404 - PDB | 0 | 200 | 1.00 | — |
| (7 days) | 20 | 80 | 0.65 | 1/4 |
|  | 20 | 100 | 0.75 | 1/5 |
|  | 40 | 50 | 0.75 | 1/3 |
|  | 40 | 60 | 0.80 | 1/2 |
|  | 40 | 80 | 0.90 | 1/2 |
|  | 80 | 0 | 1.00 | — |

The ratios of BBIT/dehydroacetic acid, sodium salt tested ranged from 1/0.02 to 1/5000.

TABLE 25

First Component (A) = N-(n-butyl)-1,2-benzisothiazolinone (BBIT)
Second Component (B) = Sodium benzoate

| Microorganism | $Q_a$ | $Q_b$ | SI | A/B |
|---|---|---|---|---|
| E. coli 8739 - M9GY | 0 | 20000 | 1.00 | — |
| (24 hours) | 20 | 20000 | 1.10 | 1/1000 |
|  | 40 | 20000 | 1.20 | 1/500 |
|  | 60 | 20000 | 1.30 | 1/333 |
|  | 80 | 20000 | 1.40 | 1/250 |
|  | 100 | 20000 | 1.50 | 1/200 |
|  | 200 | 0 | 1.00 | — |
| C. albicans 10231 - PDB | 0 | 2000 | 1.00 | — |
| (48 hours) | 2.5 | 400 | 0.53 | 1/160 |
|  | 2.5 | 500 | 0.58 | 1/200 |
|  | 2.5 | 600 | 0.63 | 1/240 |
|  | 2.5 | 800 | 0.73 | 1/320 |
|  | 2.5 | 1000 | 0.83 | 1/400 |
|  | 5 | 300 | 0.82 | 1/60 |
|  | 5 | 400 | 0.87 | 1/80 |
|  | 5 | 500 | 0.92 | 1/100 |
|  | 5 | 600 | 0.97 | 1/120 |
|  | 7.5 | 0 | 1.00 | — |
| A. niger 16404 - PDB | 0 | 10000 | 1.00 | — |
| (7 days) | 5 | 8000 | 0.86 | 1/1600 |
|  | 10 | 3000 | 0.43 | 1/300 |
|  | 10 | 4000 | 0.53 | 1/400 |
|  | 10 | 5000 | 0.63 | 1/500 |
|  | 10 | 6000 | 0.73 | 1/600 |
|  | 10 | 8000 | 0.93 | 1/800 |
|  | 15 | 3000 | 0.49 | 1/200 |
|  | 15 | 4000 | 0.59 | 1/267 |
|  | 15 | 5000 | 0.69 | 1/333 |
|  | 15 | 6000 | 0.79 | 1/400 |
|  | 15 | 7000 | 0.89 | 1/467 |
|  | 15 | 8000 | 0.99 | 1/533 |
|  | 20 | 1000 | 0.35 | 1/50 |
|  | 20 | 2000 | 0.45 | 1/100 |
|  | 20 | 3000 | 0.55 | 1/150 |
|  | 20 | 4000 | 0.65 | 1/200 |
|  | 20 | 5000 | 0.75 | 1/250 |
|  | 20 | 6000 | 0.85 | 1/300 |
|  | 20 | 7000 | 0.95 | 1/350 |
|  | 40 | 500 | 0.55 | 1/13 |
|  | 40 | 600 | 0.56 | 1/15 |
|  | 40 | 800 | 0.58 | 1/20 |
|  | 40 | 1000 | 0.60 | 1/25 |

TABLE 25-continued

First Component (A) = N-(n-butyl)-1,2-benzisothiazolinone (BBIT)
Second Component (B) = Sodium benzoate

| Microorganism | $Q_a$ | $Q_b$ | SI | A/B |
|---|---|---|---|---|
| | 40 | 2000 | 0.70 | 1/50 |
| | 40 | 3000 | 0.80 | 1/75 |
| | 40 | 4000 | 0.90 | 1/100 |
| | 80 | 0 | 1.00 | — |

The ratios of BBIT/sodium benzoate tested ranged from 1/0.2 to 1/5000.

TABLE 26

First Component (A) = N-(n-butyl)-1,2-benzisothiazolinone (BBIT)
Second Component (B) = Sodium citrate

| Microorganism | $Q_a$ | $Q_b$ | SI | A/B |
|---|---|---|---|---|
| E. coli 8739 - M9GY | 0 | 20000 | 1.00 | — |
| (24 hours) | 20 | 20000 | 1.10 | 1/1000 |
| | 40 | 20000 | 1.20 | 1/500 |
| | 60 | 20000 | 1.30 | 1/333 |
| | 80 | 20000 | 1.40 | 1/250 |
| | 100 | 20000 | 1.50 | 1/200 |
| | 200 | 0 | 1.00 | — |
| C. albicans 10231 - PDB | 0 | 10000 | 1.00 | — |
| (48 hours) | 2.5 | 3000 | 0.55 | 1/1200 |
| | 2.5 | 4000 | 0.65 | 1/1600 |
| | 2.5 | 5000 | 0.75 | 1/2000 |
| | 2.5 | 6000 | 0.85 | 1/2400 |
| | 5 | 600 | 0.56 | 1/120 |
| | 5 | 800 | 0.58 | 1/160 |
| | 5 | 1000 | 0.60 | 1/200 |
| | 5 | 2000 | 0.70 | 1/400 |
| | 5 | 3000 | 0.80 | 1/600 |
| | 5 | 4000 | 0.90 | 1/800 |
| | 10 | 0 | 1.00 | — |
| A. niger 16404 - PDB | 0 | 10000 | 1.00 | — |
| (3 days) | 5 | 8000 | 0.93 | 1/1600 |
| | 10 | 5000 | 0.75 | 1/500 |
| | 10 | 6000 | 0.85 | 1/600 |
| | 15 | 3000 | 0.68 | 1/200 |
| | 15 | 4000 | 0.78 | 1/267 |
| | 15 | 5000 | 0.88 | 1/333 |
| | 15 | 6000 | 0.98 | 1/400 |
| | 20 | 1000 | 0.60 | 1/50 |
| | 20 | 2000 | 0.70 | 1/100 |
| | 20 | 3000 | 0.80 | 1/150 |
| | 20 | 4000 | 0.90 | 1/200 |
| | 40 | 0 | 1.00 | — |

The ratios of BBIT/sodium citrate tested ranged from 1/0.2 to 1/5000.

TABLE 27

First Component (A) = N-methyl-1,2-benzisothiazolin-3-one (MBIT)
Second Component (B) = N-(n-butyl)-1,2-benzisothiazolinone (BBIT)

| Microorganism | $Q_a$ | $Q_b$ | SI | A/B |
|---|---|---|---|---|
| E. coli 8739 - M9GY | 0 | 100 | 1.00 | — |
| (24 hours) | 2.5 | 50 | 0.75 | 1/20 |
| | 2.5 | 60 | 0.85 | 1/24 |
| | 5 | 40 | 0.90 | 1/8 |
| | 7.5 | 10 | 0.85 | 1/1 |
| | 7.5 | 20 | 0.95 | 1/3 |
| | 10 | 0 | 1.00 | — |
| C. albicans 10231 - PDB | 0 | 6 | 1.00 | — |
| (48 hours) | 2.5 | 3 | 0.75 | 1/1 |
| | 2.5 | 4 | 0.92 | 1/2 |
| | 10 | 0 | 1.00 | — |
| A. niger 16404 - PDB | 0 | 40 | 1.00 | — |
| (4 days) | 10 | 5 | 0.38 | 1/0.5 |
| | 10 | 6 | 0.40 | 1/0.6 |
| | 10 | 8 | 0.45 | 1/0.8 |
| | 10 | 10 | 0.50 | 1/1 |
| | 10 | 20 | 0.75 | 1/2 |
| | 20 | 6 | 0.65 | 1/0.3 |
| | 20 | 8 | 0.70 | 1/0.4 |
| | 20 | 10 | 0.75 | 1/0.5 |
| | 40 | 0 | 1.00 | — |

The ratios of MBIT/BBIT tested ranged from 1/0.01 to 1/400.

TABLE 28

First Component (A) = N-methyl-1,2-benzisothiazolin-3-one (MBIT)
Second Component (B) = Benzalkonium chloride (Hyamine 3500)

| Microorganism | $Q_a$ | $Q_b$ | SI | A/B |
|---|---|---|---|---|
| E. coli 8739 - M9GY | 0 | 10 | 1.00 | — |
| (24 hours) | 2.5 | 4 | 1.25 | 1/2 |
| | 5 | 3 | 1.25 | 1/0.6 |
| | 7.5 | 3 | 1.50 | 1/0.4 |
| | 100 | 0 | 1.00 | — |
| C. albicans 10231 - PDB | 0 | 60 | 1.00 | — |
| (24 hours) | 2 | 10 | 0.42 | 1/5 |
| | 2 | 20 | 0.58 | 1/10 |
| | 2 | 30 | 0.75 | 1/15 |
| | 2 | 40 | 0.92 | 1/20 |
| | 4 | 3 | 0.55 | 1/0.8 |
| | 4 | 4 | 0.57 | 1/1 |
| | 4 | 5 | 0.58 | 1/1 |
| | 4 | 6 | 0.60 | 1/2 |
| | 4 | 8 | 0.63 | 1/2 |
| | 4 | 10 | 0.67 | 1/3 |
| | 4 | 20 | 0.83 | 1/5 |
| | 6 | 3 | 0.80 | 1/0.5 |
| | 6 | 4 | 0.82 | 1/0.7 |
| | 6 | 5 | 0.83 | 1/0.9 |
| | 6 | 6 | 0.85 | 1/1 |
| | 6 | 8 | 0.88 | 1/1 |
| | 6 | 10 | 0.92 | 1/2 |
| | 8 | 0 | 1.00 | — |
| A. niger 16404 - PDB | 0 | 200 | 1.00 | — |
| (4 days) | 10 | 30 | 0.48 | 1/3 |
| | 10 | 40 | 0.53 | 1/4 |
| | 10 | 50 | 0.58 | 1/5 |
| | 10 | 60 | 0.63 | 1/6 |
| | 10 | 80 | 0.73 | 1/8 |
| | 10 | 100 | 0.83 | 1/10 |
| | 20 | 4 | 0.69 | 1/0.2 |
| | 20 | 5 | 0.69 | 1/0.3 |
| | 20 | 6 | 0.70 | 1/0.3 |
| | 20 | 8 | 0.71 | 1/0.4 |
| | 20 | 10 | 0.72 | 1/0.5 |
| | 20 | 20 | 0.77 | 1/4 |
| | 20 | 30 | 0.82 | 1/1.5 |
| | 20 | 40 | 0.87 | 1/2 |
| | 20 | 50 | 0.92 | 1/3 |
| | 20 | 60 | 0.97 | 1/3 |
| | 30 | 0 | 1.00 | — |

The ratios of MBIT/benzalkonium chloride tested ranged from 1/0.01 to 1/400.

TABLE 29

First Component (A) = N-methyl-1,2-benzisothiazolin-3-one (MBIT)
Second Component (B) = Benzethonium chloride (Hyamine 1622)

| Microorganism | $Q_a$ | $Q_b$ | SI | A/B |
|---|---|---|---|---|
| E. coli 8739 - M9GY | 0 | 20 | 1.00 | — |
| (24 hours) | 2.5 | 20 | 1.25 | 1/8 |
| | 5 | 20 | 1.50 | 1/4 |
| | 7.5 | 5 | 1.00 | 1/0.7 |
| | 10 | 0 | 1.00 | — |

TABLE 29-continued

First Component (A) = N-methyl-1,2-benzisothiazolin-3-one (MBIT)
Second Component (B) = Benzethonium chloride (Hyamine 1622)

| Microorganism | $Q_a$ | $Q_b$ | SI | A/B |
|---|---|---|---|---|
| C. albicans 10231 - PDB | 0 | 4 | 1.00 | — |
| (24 hours) | 2 | 3 | 1.00 | 1/2 |
|  | 4 | 3 | 1.25 | 1/0.8 |
|  | 6 | 1 | 1.00 | 1/0.2 |
|  | 8 | 0 | 1.00 | — |
| A. niger 16404 - PDB | 0 | 10 | 1.00 | — |
| (4 days) | 10 | 4 | 0.73 | 1/0.4 |
|  | 10 | 5 | 0.83 | 1/0.5 |
|  | 10 | 6 | 0.93 | 1/0.6 |
|  | 30 | 0 | 1.00 | — |

The ratios of MBIT/benzethonium chloride tested ranged from 1/0.01 to 1/400.

TABLE 30

First Component (A) = N-methyl-1,2-benzisothiazolin-3-one (MBIT)
Second Component (B) = Benzyl alcohol

| Microorganism | $Q_a$ | $Q_b$ | SI | A/B |
|---|---|---|---|---|
| E. coli 8739 - M9GY | 0 | 5000 | 1.00 | — |
| (24 hours) | 2.5 | 5000 | 1.25 | 1/2000 |
|  | 5 | 4000 | 1.30 | 1/800 |
|  | 7.5 | 4000 | 1.55 | 1/533 |
|  | 10 | 0 | 1.00 | — |
| C. albicans 10231 - PDB | 0 | 4000 | 1.00 | — |
| (48 hours) | 2.5 | 2000 | 0.75 | 1/800 |
|  | 5 | 500 | 0.63 | 1/100 |
|  | 5 | 1000 | 0.75 | 1/200 |
|  | 7.5 | 40 | 0.76 | 1/5 |
|  | 7.5 | 50 | 0.76 | 1/7 |
|  | 7.5 | 60 | 0.77 | 1/8 |
|  | 7.5 | 80 | 0.77 | 1/11 |
|  | 7.5 | 100 | 0.78 | 1/13 |
|  | 7.5 | 200 | 0.80 | 1/27 |
|  | 7.5 | 300 | 0.08 | 1/40 |
|  | 7.5 | 400 | 0.85 | 1/53 |
|  | 7.5 | 500 | 0.88 | 1/67 |
|  | 7.5 | 600 | 0.90 | 1/80 |
|  | 7.5 | 800 | 0.95 | 1/107 |
|  | 10 | 0 | 1.00 | — |
| A. niger 16404 - PDB | 0 | 6000 | 1.00 | — |
| (4 days) | 10 | 6000 | 1.20 | 1/600 |
|  | 20 | 6000 | 1.40 | 1/300 |
|  | 30 | 4000 | 1.27 | 1/133 |
|  | 50 | 0 | 1.00 | — |

The ratios of MBIT/benzyl alcohol tested ranged from 1/0.1 to 1/4000.

TABLE 31

First Component (A) = N-methyl-1,2-benzisothiazolin-3-one (MBIT)
Second Component (B) = Benzisothiazolinone (BIT)

| Microorganism | $Q_a$ | $Q_b$ | SI | A/B |
|---|---|---|---|---|
| E. coli 8739 - M9GY | 0 | 20 | 1.00 | — |
| (24 hours) | 2.5 | 10 | 0.75 | 1/4 |
|  | 5 | 5 | 0.75 | 1/1 |
|  | 5 | 6 | 0.80 | 1/1 |
|  | 5 | 8 | 0.90 | 1/2 |
|  | 7.5 | 3 | 0.90 | 1/0.4 |
|  | 7.5 | 4 | 0.95 | 1/0.5 |
|  | 10 | 0 | 1.00 | — |
| C. albicans 10231 - PDB | 0 | 30 | 1.00 | — |
| (48 hours) | 2.5 | 10 | 0.58 | 1/4 |
|  | 2.5 | 20 | 0.92 | 1/8 |
|  | 5 | 4 | 0.63 | 1/0.8 |
|  | 5 | 5 | 0.67 | 1/1 |
|  | 5 | 6 | 0.70 | 1/1 |
|  | 5 | 8 | 0.77 | 1/2 |
|  | 5 | 10 | 0.83 | 1/2 |

TABLE 31-continued

First Component (A) = N-methyl-1,2-benzisothiazolin-3-one (MBIT)
Second Component (B) = Benzisothiazolinone (BIT)

| Microorganism | $Q_a$ | $Q_b$ | SI | A/B |
|---|---|---|---|---|
|  | 7.5 | 2 | 0.82 | 1/0.3 |
|  | 7.5 | 3 | 0.85 | 1/0.4 |
|  | 7.5 | 4 | 0.88 | 1/0.5 |
|  | 7.5 | 5 | 0.92 | 1/0.7 |
|  | 7.5 | 6 | 0.95 | 1/0.8 |
|  | 10 | 0 | 1.00 | — |
| A. niger 16404 - PDB | 0 | 300 | 1.00 | — |
| (7 days) | 10 | 100 | 0.53 | 1/10 |
|  | 10 | 200 | 0.87 | 1/20 |
|  | 20 | 30 | 0.50 | 1/2 |
|  | 20 | 40 | 0.53 | 1/2 |
|  | 20 | 50 | 0.57 | 1/3 |
|  | 20 | 60 | 0.60 | 1/3 |
|  | 20 | 80 | 0.67 | 1/4 |
|  | 20 | 100 | 0.73 | 1/5 |
|  | 30 | 20 | 0.67 | 1/0.7 |
|  | 30 | 30 | 0.70 | 1/1 |
|  | 30 | 40 | 0.73 | 1/1 |
|  | 30 | 50 | 0.77 | 1/2 |
|  | 30 | 60 | 0.80 | 1/2 |
|  | 30 | 80 | 0.87 | 1/3 |
|  | 30 | 100 | 0.93 | 1/3 |
|  | 50 | 0 | 1.00 | — |

The ratios of MBIT/benzisothiazolinone tested ranged from 1/0.01 to 1/400.

TABLE 32

First Component (A) = N-methyl-1,2-benzisothiazolin-3-one (MBIT)
Second Component (B) = 2-bromo-2-nitro-propane-1,3-diol (BNPD)

| Microorganism | $Q_a$ | $Q_b$ | SI | A/B |
|---|---|---|---|---|
| E. coli 8739 - M9GY | 0 | 8 | 1.00 | — |
| (24 hours) | 2.5 | 5 | 0.88 | 1/2 |
|  | 5 | 1 | 0.63 | 1/0.2 |
|  | 5 | 2 | 0.75 | 1/0.4 |
|  | 5 | 3 | 0.88 | 1/0.6 |
|  | 7.5 | 1 | 0.88 | 1/0.1 |
|  | 7.5 | 2 | 1.00 | 1/0.3 |
|  | 10 | 0 | 1.00 | — |
| C. albicans 10231 - PDB | 0 | 1000 | 1.00 | — |
| (24 hours) | 4 | 100 | 0.60 | 1/25 |
|  | 4 | 200 | 0.70 | 1/50 |
|  | 4 | 300 | 0.80 | 1/75 |
|  | 4 | 400 | 0.90 | 1/100 |
|  | 6 | 4 | 0.75 | 1/0.7 |
|  | 6 | 5 | 0.76 | 1/0.8 |
|  | 6 | 6 | 0.76 | 1/1 |
|  | 6 | 8 | 0.76 | 1/1 |
|  | 6 | 10 | 0.76 | 1/2 |
|  | 6 | 20 | 0.77 | 1/3 |
|  | 6 | 30 | 0.78 | 1/5 |
|  | 6 | 40 | 0.79 | 1/7 |
|  | 6 | 50 | 0.80 | 1/8 |
|  | 6 | 60 | 0.81 | 1/10 |
|  | 6 | 80 | 0.83 | 1/13 |
|  | 6 | 100 | 0.85 | 1/17 |
|  | 6 | 200 | 0.95 | 1/33 |
|  | 8 | 0 | 1.00 | — |
| A. niger 16404 - PDB | 0 | 2000 | 1.00 | — |
| (4 days) | 10 | 800 | 0.60 | 0/80 |
|  | 10 | 1000 | 0.70 | 1/100 |
|  | 20 | 5 | 0.40 | 1/0.3 |
|  | 20 | 6 | 0.40 | 1/0.3 |
|  | 20 | 8 | 0.40 | 1/0.4 |
|  | 20 | 10 | 0.41 | 1/0.5 |
|  | 20 | 20 | 0.41 | 1/1 |
|  | 20 | 30 | 0.42 | 1/2 |
|  | 20 | 40 | 0.42 | 1/2 |
|  | 20 | 50 | 0.43 | 1/3 |
|  | 20 | 60 | 0.43 | 1/3 |
|  | 20 | 80 | 0.44 | 1/4 |
|  | 20 | 100 | 0.45 | 1/5 |
|  | 20 | 200 | 0.50 | 1/10 |

TABLE 32-continued

First Component (A) = N-methyl-1,2-benzisothiazolin-3-one (MBIT)
Second Component (B) = 2-bromo-2-nitro-propane-1,3-diol (BNPD)

| Microorganism | $Q_a$ | $Q_b$ | SI | A/B |
|---|---|---|---|---|
| | 20 | 300 | 0.55 | 1/15 |
| | 20 | 400 | 0.60 | 1/20 |
| | 20 | 500 | 0.65 | 1/25 |
| | 20 | 600 | 0.70 | 1/30 |
| | 20 | 800 | 0.80 | 1/40 |
| | 20 | 1000 | 0.90 | 1/50 |
| | 30 | 0 | 1.00 | — |

The ratios of MBIT/2-bromo-2-nitro-propane-1,3-diol tested ranged from 1/0.01 to 1/400.

TABLE 33

First Component (A) = N-methyl-1,2-benzisothiazolin-3-one (MBIT)
Second Component (B) = Butylene glycol

| Microorganism | $Q_a$ | $Q_b$ | SI | A/B |
|---|---|---|---|---|
| E. coli 8739 - M9GY | 0 | 20000 | 1.00 | — |
| (24 hours) | 2.5 | 20000 | 1.33 | 1/8000 |
| | 5 | 20000 | 1.67 | 1/4000 |
| | 7.5 | 0 | 1.00 | — |
| C. albicans 10231 - PDB | 0 | 20000 | 1.00 | — |
| (72 hours) | 8 | 100 | 0.81 | 1/13 |
| | 8 | 200 | 0.81 | 1/25 |
| | 8 | 300 | 0.82 | 1/38 |
| | 8 | 400 | 0.82 | 1/50 |
| | 8 | 500 | 0.83 | 1/63 |
| | 8 | 600 | 0.83 | 1/75 |
| | 8 | 800 | 0.84 | 1/100 |
| | 8 | 1000 | 0.85 | 1/125 |
| | 8 | 2000 | 0.90 | 1/250 |
| | 8 | 3000 | 0.95 | 1/375 |
| | 10 | 0 | 1.00 | — |
| A. niger 16404 - PDB | 0 | 10000 | 1.00 | — |
| (7 days) | 10 | 10000 | 1.25 | 1/1000 |
| | 20 | 10000 | 1.50 | 1/500 |
| | 30 | 10000 | 1.75 | 1/333 |
| | 40 | 0 | 1.00 | — |

The ratios of MBIT/butylene glycol tested ranged from 1/0.1 to 1/4000.

TABLE 34

First Component (A) = N-methyl-1,2-benzisothiazolin-3-one (MBIT)
Second Component (B) = Caprylyl glycol

| Microorganism | $Q_a$ | $Q_b$ | SI | A/B |
|---|---|---|---|---|
| E. coli 8739 - M9GY | 0 | 2000 | 1.00 | — |
| (24 hours) | 2.5 | 2000 | 1.25 | 1/800 |
| | 5 | 2000 | 1.50 | 1/400 |
| | 7.5 | 2000 | 1.75 | 1/267 |
| | 10 | 0 | 1.00 | — |
| C. albicans 10231 - PDB | 0 | 4000 | 1.00 | — |
| (24 hours) | 2 | 2000 | 0.70 | 1/1000 |
| | 2 | 3000 | 0.95 | 1/1500 |
| | 4 | 2000 | 0.90 | 1/500 |
| | 6 | 600 | 0.75 | 1/100 |
| | 6 | 800 | 0.80 | 1/133 |
| | 6 | 1000 | 0.85 | 1/167 |
| | 8 | 200 | 0.85 | 1/25 |
| | 8 | 300 | 0.88 | 1/38 |
| | 8 | 400 | 0.90 | 1/50 |
| | 8 | 500 | 0.93 | 1/63 |
| | 8 | 600 | 0.95 | 1/75 |
| | 10 | 0 | 1.00 | — |
| A. niger 16404 - PDB | 0 | 1000 | 1.00 | — |
| (4 days) | 10 | 1000 | 0.58 | 1/100 |
| | 10 | 2000 | 0.83 | 1/200 |
| | 20 | 1000 | 0.92 | 1/50 |
| | 20 | 0 | 1.00 | — |

The ratios of MBIT/caprylyl glycol tested ranged from 1/0.1 to 1/4000.

TABLE 35

First Component (A) = N-methyl-1,2-benzisothiazolin-3-one (MBIT)
Second Component (B) = Chlorphenesin

| Microorganism | $Q_a$ | $Q_b$ | SI | A/B |
|---|---|---|---|---|
| E. coli 8739 - M9GY | 0 | 2000 | 1.00 | — |
| (24 hours) | 7.5 | 800 | 0.90 | 1/107 |
| | 15 | 0 | 1.00 | — |
| C. albicans 10231 - PDB | 0 | 2000 | 1.00 | — |
| (72 hours) | 4 | 200 | 0.50 | 1/50 |
| | 4 | 300 | 0.55 | 1/75 |
| | 4 | 400 | 0.60 | 1/100 |
| | 4 | 500 | 0.65 | 1/125 |
| | 4 | 600 | 0.70 | 1/150 |
| | 4 | 800 | 0.80 | 1/200 |
| | 4 | 1000 | 0.90 | 1/250 |
| | 6 | 80 | 0.64 | 1/13 |
| | 6 | 100 | 0.65 | 1/17 |
| | 6 | 200 | 0.70 | 1/33 |
| | 6 | 300 | 0.75 | 1/50 |
| | 6 | 400 | 0.80 | 1/67 |
| | 6 | 500 | 0.85 | 1/83 |
| | 6 | 600 | 0.90 | 1/100 |
| | 8 | 40 | 0.82 | 1/5 |
| | 8 | 50 | 0.83 | 1/6 |
| | 8 | 60 | 0.83 | 1/8 |
| | 8 | 80 | 0.84 | 1/10 |
| | 8 | 100 | 0.85 | 1/13 |
| | 8 | 200 | 0.90 | 1/25 |
| | 8 | 300 | 0.95 | 1/38 |
| | 10 | 0 | 1.00 | — |
| A. niger 16404 - PDB | 0 | 2000 | 1.00 | — |
| (3 days) | 10 | 2000 | 1.50 | 1/200 |
| | 20 | 0 | 1.00 | — |

The ratios of MBIT/chlorphenesin tested ranged from 1/0.1 to 1/4000.

TABLE 36

First Component (A) = N-methyl-1,2-benzisothiazolin-3-one (MBIT)
Second Component (B) = DMDM Hydantoin (DMDMH)

| Microorganism | $Q_a$ | $Q_b$ | SI | A/B |
|---|---|---|---|---|
| E. coli 8739 - M9GY | 0 | 50 | 1.00 | — |
| (24 hours) | 2.5 | 60 | 1.45 | 1/24 |
| | 5 | 30 | 1.10 | 1/6 |
| | 7.5 | 10 | 0.95 | 1/1 |
| | 10 | 0 | 1.00 | — |
| C. albicans 10231 - PDB | 0 | 3000 | 1.00 | — |
| (24 hours) | 2.5 | 3000 | 1.33 | 1/1200 |
| | 5 | 1000 | 1.00 | 1/200 |
| | 7.5 | 0 | 1.00 | — |
| A. niger 16404 - PDB | 0 | 1000 | 1.00 | — |
| (3 days) | 10 | 2000 | 2.25 | 1/200 |
| | 20 | 2000 | 2.50 | 1/100 |
| | 40 | 0 | 1.00 | — |

The ratios of MBIT/DMDM Hydantoin tested ranged from 1/0.1 to 1/4000.
No synergy was observed between MBIT and DMDM Hydantoin.

TABLE 37

First Component (A) = N-methyl-1,2-benzisothiazolin-3-one (MBIT)
Second Component (B) = dithio-2,2'-bis(N-methylbenzamide) (DTBMA)

| Microorganism | $Q_a$ | $Q_b$ | SI | A/B |
|---|---|---|---|---|
| E. coli 8739 - M9GY | 0 | 80 | 1.00 | — |
| (24 hours) | 2.5 | 20 | 0.42 | 1/8 |
| | 2.5 | 30 | 0.54 | 1/12 |
| | 2.5 | 40 | 0.67 | 1/16 |
| | 2.5 | 50 | 0.79 | 1/20 |
| | 2.5 | 60 | 0.92 | 1/24 |
| | 5 | 20 | 0.58 | 1/4 |
| | 5 | 30 | 0.71 | 1/6 |

TABLE 37-continued

First Component (A) = N-methyl-1,2-benzisothiazolin-3-one (MBIT)
Second Component (B) = dithio-2,2'-bis(N-methylbenzamide) (DTBMA)

| Microorganism | $Q_a$ | $Q_b$ | SI | A/B |
|---|---|---|---|---|
|  | 5 | 40 | 0.83 | 1/8 |
|  | 5 | 50 | 0.96 | 1/10 |
|  | 7.5 | 3 | 0.54 | 1/0.4 |
|  | 7.5 | 4 | 0.55 | 1/0.5 |
|  | 7.5 | 5 | 0.56 | 1/0.7 |
|  | 7.5 | 6 | 0.58 | 1/0.8 |
|  | 7.5 | 8 | 0.60 | 1/1 |
|  | 7.5 | 10 | 0.63 | 1/1 |
|  | 7.5 | 20 | 0.75 | 1/3 |
|  | 7.5 | 30 | 0.88 | 1/4 |
|  | 10 | 1 | 0.68 | 1/0.1 |
|  | 10 | 2 | 0.69 | 1/0.2 |
|  | 10 | 3 | 0.70 | 1/0.3 |
|  | 10 | 4 | 0.72 | 1/0.4 |
|  | 10 | 5 | 0.73 | 1/0.5 |
|  | 10 | 6 | 0.74 | 1/0.6 |
|  | 10 | 8 | 0.77 | 1/0.8 |
|  | 10 | 10 | 0.79 | 1/1 |
|  | 10 | 20 | 0.92 | 1/2 |
|  | 15 | 0 | 1.00 | — |
| C. albicans 10231 - PDB | 0 | 2000 | 1.00 | — |
| (24 hours) | 6 | 60 | 0.63 | 1/10 |
|  | 6 | 80 | 0.64 | 1/13 |
|  | 6 | 100 | 0.65 | 1/17 |
|  | 6 | 200 | 0.70 | 1/33 |
|  | 6 | 300 | 0.75 | 1/50 |
|  | 6 | 400 | 0.80 | 1/67 |
|  | 6 | 500 | 0.85 | 1/83 |
|  | 6 | 600 | 0.90 | 1/100 |
|  | 8 | 10 | 0.81 | 1/1 |
|  | 8 | 20 | 0.81 | 1/3 |
|  | 8 | 30 | 0.82 | 1/4 |
|  | 8 | 40 | 0.82 | 1/5 |
|  | 8 | 50 | 0.83 | 1/6 |
|  | 8 | 60 | 0.83 | 1/8 |
|  | 8 | 80 | 0.84 | 1/10 |
|  | 8 | 100 | 0.85 | 1/13 |
|  | 8 | 200 | 0.90 | 1/25 |
|  | 8 | 300 | 0.95 | 1/38 |
|  | 10 | 0 | 1.00 | — |
| A. niger 16404 - PDB | 0 | 800 | 1.00 | — |
| (3 days) | 10 | 500 | 0.96 | 1/50 |
|  | 30 | 0 | 1.00 | — |

The ratios of MBIT/dithio-2,2'-bis(N-methylbenzamide) tested ranged from 1/0.01 to 1/400.

TABLE 38

First Component (A) = N-methyl-1,2-benzisothiazolin-3-one (MBIT)
Second Component (B) = Ethylenediamine tetraacetic acid (EDTA)

| Microorganism | $Q_a$ | $Q_b$ | SI | A/B |
|---|---|---|---|---|
| E. coli 8739 - M9GY | 0 | 40000 | 1.00 | — |
| (24 hours) | 5 | 1600 | 0.54 | 1/320 |
|  | 10 | 0 | 1.00 | — |
| C. albicans 10231 - PDB | 0 | 1000 | 1.00 | — |
| (48 hours) | 2.5 | 60 | 0.43 | 1/24 |
|  | 2.5 | 80 | 0.47 | 1/32 |
|  | 2.5 | 100 | 0.50 | 1/40 |
|  | 2.5 | 120 | 0.53 | 1/48 |
|  | 7.5 | 0 | 1.00 | — |
| A. niger 16404 - PDB | 0 | 1600 | 1.00 | — |
| (3 days) | 10 | 800 | 0.75 | 1/80 |
|  | 10 | 1000 | 0.88 | 1/100 |
|  | 20 | 200 | 0.63 | 1/10 |
|  | 20 | 400 | 0.75 | 1/20 |
|  | 20 | 600 | 0.88 | 1/30 |
|  | 40 | 0 | 1.00 | — |

The ratios of MBIT/ethylenediamine tetraacetic acid tested ranged from 1/0.3 to 1/8000.

TABLE 39

First Component (A) = N-methyl-1,2-benzisothiazolin-3-one (MBIT)
Second Component (B) = Ethylparaben

| Microorganism | $Q_a$ | $Q_b$ | SI | A/B |
|---|---|---|---|---|
| E. coli 8739 - M9GY | 0 | 2000 | 1.00 | — |
| (24 hours) | 2.5 | 2000 | 1.25 | 1/800 |
|  | 5 | 2000 | 1.50 | 1/400 |
|  | 7.5 | 400 | 0.95 | 1/53 |
|  | 10 | 0 | 1.00 | — |
| C. albicans 10231 - PDB | 0 | 2000 | 1.00 | — |
| (24 hours) | 2.5 | 600 | 0.63 | 1/240 |
|  | 2.5 | 800 | 0.73 | 1/320 |
|  | 2.5 | 1000 | 0.83 | 1/400 |
|  | 2.5 | 2000 | 1.33 | 1/800 |
|  | 5 | 50 | 0.69 | 1/10 |
|  | 5 | 60 | 0.70 | 1/12 |
|  | 5 | 80 | 0.71 | 1/16 |
|  | 5 | 100 | 0.72 | 1/20 |
|  | 5 | 200 | 0.77 | 1/40 |
|  | 5 | 300 | 0.82 | 1/60 |
|  | 5 | 400 | 0.87 | 1/80 |
|  | 5 | 500 | 0.92 | 1/100 |
|  | 5 | 600 | 0.97 | 1/120 |
|  | 7.5 | 0 | 1.00 | — |
| A. niger 16404 - PDB | 0 | 800 | 1.00 | — |
| (7 days) | 30 | 200 | 0.85 | 1/7 |
|  | 30 | 300 | 0.98 | 1/10 |
|  | 50 | 0 | 1.00 | — |

The ratios of MBIT/ethylparaben tested ranged from 1/0.1 to 1/4000.

TABLE 40

First Component (A) = N-methyl-1,2-benzisothiazolin-3-one (MBIT)
Second Component (B) = Hexamidine diisethionate

| Microorganism | $Q_a$ | $Q_b$ | SI | A/B |
|---|---|---|---|---|
| E. coli 8739 - M9GY | 0 | 8 | 1.00 | — |
| (24 hours) | 2.5 | 8 | 1.17 | 1/3 |
|  | 5 | 8 | 1.33 | 1/2 |
|  | 7.5 | 5 | 1.13 | 1/0.7 |
|  | 10 | 3 | 1.04 | 1/0.3 |
|  | 15 | 0 | 1.00 | — |
| C. albicans 10231 - PDB | 0 | 10 | 1.00 | — |
| (24 hours) | 2 | 5 | 0.70 | 1/3 |
|  | 2 | 6 | 0.80 | 1/3 |
|  | 4 | 4 | 0.80 | 1/1 |
|  | 4 | 5 | 0.90 | 1/1 |
|  | 8 | 1 | 0.90 | 1/0.1 |
|  | 10 | 0 | 1.00 | — |

The ratios of MBIT/hexamidine diisethionate tested ranged from 1/0.01 to 1/400.

TABLE 41

First Component (A) = N-methyl-1,2-benzisothiazolin-3-one (MBIT)
Second Component (B) = Hexetidine

| Microorganism | $Q_a$ | $Q_b$ | SI | A/B |
|---|---|---|---|---|
| E. coli 8739 - M9GY | 0 | 80 | 1.00 | — |
| (72 hours) | 5 | 40 | 0.83 | 1/8 |
|  | 5 | 50 | 0.96 | 1/10 |
|  | 15 | 0 | 1.00 | — |
| C. albicans 10231 - PDB | 0 | 80 | 1.00 | — |
| (72 hours) | 2 | 40 | 0.53 | 1/20 |
|  | 2 | 50 | 0.63 | 1/25 |
|  | 2 | 60 | 0.73 | 1/30 |
|  | 2 | 80 | 0.93 | 1/40 |
|  | 4 | 30 | 0.57 | 1/8 |
|  | 4 | 40 | 0.67 | 1/10 |
|  | 4 | 50 | 0.77 | 1/13 |
|  | 4 | 60 | 0.87 | 1/15 |
|  | 6 | 20 | 0.60 | 1/3 |
|  | 6 | 30 | 0.70 | 1/5 |

TABLE 41-continued

First Component (A) = N-methyl-1,2-benzisothiazolin-3-one (MBIT)
Second Component (B) = Hexetidine

| Microorganism | $Q_a$ | $Q_b$ | SI | A/B |
|---|---|---|---|---|
|  | 6 | 40 | 0.80 | 1/7 |
|  | 6 | 50 | 0.90 | 1/8 |
|  | 8 | 5 | 0.58 | 1/0.6 |
|  | 8 | 6 | 0.59 | 1/0.7 |
|  | 8 | 8 | 0.61 | 1/1 |
|  | 8 | 10 | 0.63 | 1/1 |
|  | 8 | 20 | 0.73 | 1/3 |
|  | 8 | 30 | 0.83 | 1/4 |
|  | 8 | 40 | 0.93 | 1/5 |
|  | 10 | 1 | 0.68 | 1/0.1 |
|  | 10 | 2 | 0.69 | 1/0.2 |
|  | 10 | 3 | 0.70 | 1/0.3 |
|  | 15 | 0 | 1.00 | — |
| A. niger 16404 - PDB | 0 | 200 | 1.00 | — |
| (3 days) | 10 | 40 | 0.53 | 1/4 |
|  | 10 | 50 | 0.58 | 1/5 |
|  | 10 | 60 | 0.63 | 1/6 |
|  | 10 | 80 | 0.73 | 1/8 |
|  | 10 | 100 | 0.83 | 1/10 |
|  | 20 | 20 | 0.77 | 1/1 |
|  | 20 | 30 | 0.82 | 1/2 |
|  | 20 | 40 | 0.87 | 1/2 |
|  | 20 | 50 | 0.92 | 1/3 |
|  | 20 | 60 | 0.97 | 1/3 |
|  | 20 | 0 | 1.00 | — |

The ratios of MBIT/hexetidine tested ranged from 1/0.01 to 1/400.

TABLE 42

First Component (A) = N-methyl-1,2-benzisothiazolin-3-one (MBIT)
Second Component (B) = Hexylene glycol

| Microorganism | $Q_a$ | $Q_b$ | SI | A/B |
|---|---|---|---|---|
| E. coli 8739 - M9GY | 0 | 20000 | 1.00 | — |
| (24 hours) | 2.5 | 20000 | 1.17 | 1/8000 |
|  | 5 | 20000 | 1.33 | 1/4000 |
|  | 7.5 | 20000 | 1.50 | 1/2667 |
|  | 10 | 20000 | 1.67 | 1/2000 |
|  | 15 | 0 | 1.00 | — |
| C. albicans 10231 - PDB | 0 | 20000 | 1.00 | — |
| (24 hours) | 2 | 20000 | 1.13 | 1/10000 |
|  | 4 | 20000 | 1.27 | 1/5000 |
|  | 6 | 20000 | 1.40 | 1/3333 |
|  | 8 | 20000 | 1.53 | 1/2500 |
|  | 10 | 20000 | 1.67 | 1/2000 |
|  | 15 | 0 | 1.00 | — |
| A. niger 16404 - PDB | 0 | 20000 | 1.00 | — |
| (3 days) | 10 | 20000 | 1.33 | 1/2000 |
|  | 20 | 20000 | 1.67 | 1/1000 |
|  | 30 | 0 | 1.00 | — |

The ratios of MBIT/hexylene glycol tested ranged from 1/0.1 to 1/10000. No synergy was observed between MBIT and hexylene glycol.

TABLE 43

First Component (A) = N-methyl-1,2-benzisothiazolin-3-one (MBIT)
Second Component (B) = Methylparaben

| Microorganism | $Q_a$ | $Q_b$ | SI | A/B |
|---|---|---|---|---|
| E. coli 8739 - M9GY | 0 | 2000 | 1.00 | — |
| (24 hours) | 2.5 | 2000 | 1.25 | 1/800 |
|  | 5 | 2000 | 1.50 | 1/400 |
|  | 7.5 | 800 | 1.15 | 1/107 |
|  | 10 | 0 | 1.00 | — |
| C. albicans 10231 - PDB | 0 | 2000 | 1.00 | — |
| (48 hours) | 2.5 | 1000 | 0.83 | 1/400 |
|  | 5 | 400 | 0.87 | 1/80 |
|  | 5 | 500 | 0.92 | 1/100 |
|  | 5 | 600 | 0.97 | 1/120 |
|  | 7.5 | 0 | 1.00 | — |

TABLE 43-continued

First Component (A) = N-methyl-1,2-benzisothiazolin-3-one (MBIT)
Second Component (B) = Methylparaben

| Microorganism | $Q_a$ | $Q_b$ | SI | A/B |
|---|---|---|---|---|
| A. niger 16404 - PDB | 0 | 800 | 1.00 | — |
| (7 days) | 30 | 50 | 0.66 | 1/2 |
|  | 30 | 60 | 0.68 | 1/2 |
|  | 30 | 80 | 0.70 | 1/3 |
|  | 30 | 100 | 0.73 | 1/6 |
|  | 30 | 200 | 0.85 | 1/7 |
|  | 30 | 300 | 0.98 | 1/10 |
|  | 50 | 0 | 1.00 | — |

The ratios of MBIT/methylparaben tested ranged from 1/0.1 to 1/4000.

TABLE 44

First Component (A) = N-methyl-1,2-benzisothiazolin-3-one (MBIT)
Second Component (B) = Pentylene glycol

| Microorganism | $Q_a$ | $Q_b$ | SI | A/B |
|---|---|---|---|---|
| E. coli 8739 - M9GY | 0 | 20000 | 1.00 | — |
| (24 hours) | 2.5 | 20000 | 1.17 | 1/8000 |
|  | 5 | 20000 | 1.33 | 1/4000 |
|  | 7.5 | 20000 | 1.50 | 1/2667 |
|  | 10 | 20000 | 1.67 | 1/2000 |
|  | 15 | 0 | 1.00 | — |
| C. albicans 10231 - PDB | 0 | 20000 | 1.00 | — |
| (24 hours) | 2 | 20000 | 1.13 | 1/10000 |
|  | 4 | 20000 | 1.27 | 1/5000 |
|  | 8 | 20000 | 1.53 | 1/2500 |
|  | 10 | 0 | 1.00 | — |
| A. niger 16404 - PDB | 0 | 20000 | 1.00 | — |
| (3 days) | 10 | 20000 | 1.67 | 1/2000 |
|  | 20 | 20000 | 2.33 | 1/1000 |
|  | 30 | 0 | 1.00 | — |

The ratios of MBIT/pentylene glycol tested ranged from 1/0.1 to 1/10000. No synergy was observed between MBIT and pentylene glycol.

TABLE 45

First Component (A) = N-methyl-1,2-benzisothiazolin-3-one (MBIT)
Second Component (B) = Phenoxyethanol

| Microorganism | $Q_a$ | $Q_b$ | SI | A/B |
|---|---|---|---|---|
| E. coli 8739 - M9GY | 0 | 4000 | 1.00 | — |
| (24 hours) | 2.5 | 4000 | 1.17 | 1/1600 |
|  | 5 | 4000 | 1.33 | 1/800 |
|  | 7.5 | 4000 | 1.50 | 1/533 |
|  | 10 | 3000 | 1.42 | 1/300 |
|  | 40 | 3000 | 3.42 | 1/75 |
|  | 15 | 0 | 1.00 | — |
| C. albicans 10231 - PDB | 0 | 3000 | 1.00 | — |
| (24 hours) | 5 | 600 | 0.87 | 1/120 |
|  | 5 | 800 | 0.93 | 1/160 |
|  | 7.5 | 0 | 1.00 | — |
| A. niger 16404 - PDB | 0 | 4000 | 1.00 | — |
| (3 days) | 10 | 4000 | 1.25 | 1/400 |
|  | 20 | 2000 | 1.00 | 1/100 |
|  | 40 | 0 | 1.00 | — |

The ratios of MBIT/phenoxyethanol tested ranged from 1/0.1 to 1/4000.

TABLE 46

First Component (A) = N-methyl-1,2-benzisothiazolin-3-one (MBIT)
Second Component (B) = linoleamidopropyl PG-dimonium chloride phosphate (Phospholipid EFA)

| Microorganism | $Q_a$ | $Q_b$ | SI | A/B |
|---|---|---|---|---|
| E. coli 8739 - M9GY | 0 | 500 | 1.00 | — |
| (48 hours) | 15 | 40 | 0.83 | 1/3 |
|  | 15 | 50 | 0.85 | 1/3 |
|  | 15 | 60 | 0.87 | 1/4 |
|  | 15 | 80 | 0.91 | 1/5 |

TABLE 46-continued

First Component (A) = N-methyl-1,2-benzisothiazolin-3-one (MBIT)
Second Component (B) = linoleamidopropyl PG-dimonium
chloride phosphate (Phospholipid EFA)

| Microorganism | $Q_a$ | $Q_b$ | SI | A/B |
|---|---|---|---|---|
| | 15 | 100 | 0.95 | 1/7 |
| | 20 | 0 | 1.00 | — |
| C. albicans 10231 - PDB (24 hours) | 0 | 1000 | 1.00 | — |
| | 2 | 800 | 0.93 | 1/400 |
| | 4 | 600 | 0.87 | 1/150 |
| | 6 | 500 | 0.90 | 1/83 |
| | 15 | 0 | 1.00 | — |
| A. niger 16404 - PDB (3 days) | 0 | 2000 | 1.00 | — |
| | 10 | 800 | 0.73 | 1/80 |
| | 10 | 1000 | 0.83 | 1/100 |
| | 20 | 300 | 0.82 | 1/15 |
| | 20 | 400 | 0.87 | 1/20 |
| | 20 | 500 | 0.92 | 1/25 |
| | 20 | 600 | 0.97 | 1/30 |
| | 30 | 0 | 1.00 | — |

The ratios of MBIT/linoleamidopropyl PG-dimonium chloride phosphate tested ranged from 1/0.01 to 1/400.

TABLE 47

First Component (A) = N-methyl-1,2-benzisothiazolin-3-one (MBIT)
Second Component (B) = cocamidopropyl PG-dimonium
chloride phosphate (Phospholipid PTC)

| Microorganism | $Q_a$ | $Q_b$ | SI | A/B |
|---|---|---|---|---|
| E. coli 8739 - M9GY (48 hours) | 0 | 100 | 1.00 | — |
| | 2.5 | 60 | 0.73 | 1/24 |
| | 2.5 | 80 | 0.93 | 1/32 |
| | 10 | 30 | 0.80 | 1/3 |
| | 10 | 40 | 0.90 | 1/4 |
| | 15 | 10 | 0.85 | 1/0.7 |
| | 15 | 20 | 0.95 | 1/1 |
| | 20 | 0 | 1.00 | — |
| C. albicans 10231 - PDB (24 hours) | 0 | 1000 | 1.00 | — |
| | 4 | 500 | 0.90 | 1/125 |
| | 6 | 300 | 0.90 | 1/50 |
| | 8 | 3 | 0.80 | 1/0.4 |
| | 8 | 4 | 0.80 | 1/0.5 |
| | 8 | 5 | 0.81 | 1/0.7 |
| | 8 | 6 | 0.81 | 1/0.8 |
| | 8 | 8 | 0.81 | 1/1 |
| | 8 | 10 | 0.81 | 1/1 |
| | 8 | 20 | 0.82 | 1/3 |
| | 8 | 30 | 0.83 | 1/4 |
| | 8 | 40 | 0.84 | 1/5 |
| | 8 | 50 | 0.85 | 1/6 |
| | 8 | 60 | 0.86 | 1/8 |
| | 8 | 80 | 0.88 | 1/10 |
| | 8 | 100 | 0.90 | 1/13 |
| | 10 | 0 | 1.00 | — |
| A. niger 16404 - PDB (4 days) | 0 | 1000 | 1.00 | — |
| | 10 | 500 | 0.83 | 1/50 |
| | 10 | 600 | 0.93 | 1/60 |
| | 30 | 0 | 1.00 | — |

The ratios of MBIT/cocamidopropyl PG-dimonium chloride phosphate tested ranged from 1/0.01 to 1/400.

TABLE 48

First Component (A) = N-methyl-1,2-benzisothiazolin-3-one (MBIT)
Second Component (B) = Potassium sorbate

| Microorganism | $Q_a$ | $Q_b$ | SI | A/B |
|---|---|---|---|---|
| E. coli 8739 - M9GY (48 hours) | 0 | 20000 | 1.00 | — |
| | 10 | 1000 | 0.72 | 1/100 |
| | 10 | 2000 | 0.77 | 1/200 |
| | 10 | 3000 | 0.82 | 1/300 |
| | 10 | 4000 | 0.87 | 1/400 |

TABLE 48-continued

First Component (A) = N-methyl-1,2-benzisothiazolin-3-one (MBIT)
Second Component (B) = Potassium sorbate

| Microorganism | $Q_a$ | $Q_b$ | SI | A/B |
|---|---|---|---|---|
| | 10 | 5000 | 0.92 | 1/500 |
| | 10 | 6000 | 0.97 | 1/600 |
| | 15 | 0 | 1.00 | — |
| C. albicans 10231 - PDB (24 hours) | 0 | 400 | 1.00 | — |
| | 2.5 | 200 | 0.83 | 1/80 |
| | 5 | 40 | 0.77 | 1/8 |
| | 5 | 50 | 0.79 | 1/10 |
| | 5 | 60 | 0.82 | 1/12 |
| | 5 | 80 | 0.87 | 1/16 |
| | 5 | 100 | 0.92 | 1/20 |
| | 7.5 | 0 | 1.00 | — |
| A. niger 16404 - PDB (4 days) | 0 | 10000 | 1.00 | — |
| | 10 | 6000 | 0.85 | 1/600 |
| | 20 | 1000 | 0.60 | 1/50 |
| | 20 | 2000 | 0.70 | 1/100 |
| | 20 | 3000 | 0.80 | 1/150 |
| | 20 | 4000 | 0.90 | 1/200 |
| | 40 | 0 | 1.00 | — |

The ratios of MBIT/potassium sorbate tested ranged from 1/0.1 to 1/4000.

TABLE 49

First Component (A) = N-methyl-1,2-benzisothiazolin-3-one (MBIT)
Second Component (B) = Propylparaben

| Microorganism | $Q_a$ | $Q_b$ | SI | A/B |
|---|---|---|---|---|
| E. coli 8739 - M9GY (48 hours) | 0 | 4000 | 1.00 | — |
| | 2.5 | 2000 | 0.67 | 1/800 |
| | 2.5 | 3000 | 0.92 | 1/1200 |
| | 5 | 2000 | 0.83 | 1/400 |
| | 15 | 0 | 1.00 | — |
| C. albicans 10231 - PDB (24 hours) | 0 | 2000 | 1.00 | — |
| | 2.5 | 800 | 0.73 | 1/320 |
| | 2.5 | 1000 | 0.83 | 1/400 |
| | 5 | 400 | 0.87 | 1/80 |
| | 5 | 500 | 0.92 | 1/100 |
| | 5 | 600 | 0.97 | 1/120 |
| | 7.5 | 0 | 1.00 | — |
| A. niger 16404 - PDB (7 days) | 0 | 2000 | 1.00 | — |
| | 10 | 800 | 0.60 | 1/80 |
| | 10 | 1000 | 0.70 | 1/100 |
| | 20 | 1000 | 0.90 | 1/50 |
| | 30 | 300 | 0.75 | 1/10 |
| | 30 | 400 | 0.80 | 1/13 |
| | 30 | 500 | 0.85 | 1/17 |
| | 30 | 600 | 0.90 | 1/20 |
| | 50 | 0 | 1.00 | — |

The ratios of MBIT/propylparaben tested ranged from 1/0.1 to 1/4000.

TABLE 50

First Component (A) = N-methyl-1,2-benzisothiazolin-3-one (MBIT)
Second Component (B) = Quaternium-15
(active-1-(3-chloroallyl)-3,5,7-triaza-1-azoniaadamantane chloride)

| Microorganism | $Q_a$ | $Q_b$ | SI | A/B |
|---|---|---|---|---|
| E. coli 8739 - M9GY (24 hours) | 0 | 50 | 1.00 | — |
| | 5 | 20 | 0.90 | 1/400 |
| | 7.5 | 2 | 0.79 | 1/0.3 |
| | 7.5 | 3 | 0.81 | 1/0.4 |
| | 7.5 | 4 | 0.83 | 1/0.5 |
| | 7.5 | 5 | 0.85 | 1/0.7 |
| | 7.5 | 6 | 0.87 | 1/0.8 |
| | 7.5 | 8 | 0.91 | 1/1 |
| | 7.5 | 10 | 0.95 | 1/1 |
| | 10 | 0 | 1.00 | — |

TABLE 50-continued

First Component (A) = N-methyl-1,2-benzisothiazolin-3-one (MBIT)
Second Component (B) = Quaternium-15
(active-1-(3-chloroallyl)-3,5,7-triaza-1-azoniaadamantane chloride)

| Microorganism | $Q_a$ | $Q_b$ | SI | A/B |
|---|---|---|---|---|
| C. albicans 10231 - PDB | 0 | 500 | 1.00 | — |
| (24 hours) | 2.5 | 500 | 1.33 | 1/200 |
|  | 5 | 300 | 1.27 | 1/60 |
|  | 7.5 | 0 | 1.00 | — |
| A. niger 16404 - PDB | 0 | 3000 | 1.00 | — |
| (3 days) | 10 | 1000 | 0.58 | 1/100 |
|  | 10 | 2000 | 0.92 | 1/200 |
|  | 20 | 1000 | 0.83 | 1/50 |
|  | 40 | 0 | 1.00 | — |

The ratios of MBIT/1-(3-chloroallyl)-3,5,7-triaza-1-azoniaadamantane chloride tested ranged from 1/0.01 to 1/4000.

TABLE 51

First Component (A) = N-methyl-1,2-benzisothiazolin-3-one (MBIT)
Second Component (B) = Dehydroacetic acid, sodium salt (SDHA)

| Microorganism | $Q_a$ | $Q_b$ | SI | A/B |
|---|---|---|---|---|
| E. coli 8739 - M9GY | 0 | 20000 | 1.00 | — |
| (24 hours) | 2.5 | 20000 | 1.25 | 1/8000 |
|  | 5 | 20000 | 1.50 | 1/4000 |
|  | 7.5 | 20000 | 1.75 | 1/2667 |
|  | 10 | 0 | 1.00 | — |
| C. albicans 10231 - PDB | 0 | 40 | 1.00 | — |
| (24 hours) | 2 | 40 | 1.25 | 1/20 |
|  | 4 | 30 | 1.25 | 1/8 |
|  | 6 | 8 | 0.95 | 1/1 |
|  | 8 | 0 | 1.00 | — |
| A. niger 16404 - PDB | 0 | 200 | 1.00 | — |
| (7 days) | 20 | 80 | 0.80 | 1/4 |
|  | 20 | 100 | 0.90 | 1/5 |
|  | 30 | 50 | 0.85 | 1/2 |
|  | 30 | 60 | 0.90 | 1/2 |
|  | 50 | 0 | 1.00 | — |

The ratios of MBIT/dehydroacetic acid, sodium salt tested ranged from 1/0.01 to 1/4000.

TABLE 52

First Component (A) = N-methyl-1,2-benzisothiazolin-3-one (MBIT)
Second Component (B) = Sodium benzoate

| Microorganism | $Q_a$ | $Q_b$ | SI | A/B |
|---|---|---|---|---|
| E. coli 8739 - M9GY | 0 | 10000 | 1.00 | — |
| (24 hours) | 2.5 | 10000 | 1.25 | 1/4000 |
|  | 5 | 10000 | 1.50 | 1/2000 |
|  | 7.5 | 10000 | 1.75 | 1/1333 |
|  | 10 | 0 | 1.00 | — |
| C. albicans 10231 - PDB | 0 | 2000 | 1.00 | — |
| (48 hours) | 2.5 | 800 | 0.65 | 1/320 |
|  | 2.5 | 1000 | 0.75 | 1/400 |
|  | 5 | 300 | 0.65 | 1/60 |
|  | 5 | 400 | 0.70 | 1/80 |
|  | 5 | 500 | 0.75 | 1/100 |
|  | 5 | 600 | 0.80 | 1/120 |
|  | 5 | 800 | 0.90 | 1/160 |
|  | 7.5 | 30 | 0.77 | 1/4 |
|  | 7.5 | 40 | 0.77 | 1/5 |
|  | 7.5 | 50 | 0.78 | 1/7 |
|  | 7.5 | 60 | 0.78 | 1/8 |
|  | 7.5 | 80 | 0.79 | 1/11 |
|  | 7.5 | 100 | 0.80 | 1/13 |
|  | 7.5 | 200 | 0.85 | 1/27 |
|  | 7.5 | 300 | 0.90 | 1/40 |
|  | 7.5 | 400 | 0.95 | 1/53 |
|  | 10 | 0 | 1.00 | — |

TABLE 52-continued

First Component (A) = N-methyl-1,2-benzisothiazolin-3-one (MBIT)
Second Component (B) = Sodium benzoate

| Microorganism | $Q_a$ | $Q_b$ | SI | A/B |
|---|---|---|---|---|
| A. niger 16404 - PDB | 0 | 10000 | 1.00 | — |
| (7 days) | 10 | 6000 | 0.77 | 1/600 |
|  | 10 | 8000 | 0.97 | 1/800 |
|  | 20 | 6000 | 0.93 | 1/300 |
|  | 30 | 2000 | 0.70 | 1/67 |
|  | 30 | 3000 | 0.80 | 1/100 |
|  | 30 | 4000 | 0.90 | 1/133 |
|  | 40 | 2000 | 0.87 | 1/50 |
|  | 40 | 3000 | 0.97 | 1/75 |
|  | 60 | 0 | 1.00 | — |

The ratios of MBIT/sodium benzoate tested ranged from 1/0.1 to 1/4000.

TABLE 53

First Component (A) = N-methyl-1,2-benzisothiazolin-3-one (MBIT)
Second Component (B) = Sodium citrate

| Microorganism | $Q_a$ | $Q_b$ | SI | A/B |
|---|---|---|---|---|
| E. coli 8739 - M9GY | 0 | 20000 | 1.00 | — |
| (24 hours) | 2.5 | 20000 | 1.25 | 1/8000 |
|  | 5 | 20000 | 1.50 | 1/4000 |
|  | 7.5 | 20000 | 1.75 | 1/2667 |
|  | 10 | 0 | 1.00 | — |
| C. albicans 10231 - PDB | 0 | 10000 | 1.00 | — |
| (24 hours) | 2.5 | 3000 | 0.63 | 1/1200 |
|  | 2.5 | 4000 | 0.73 | 1/1600 |
|  | 2.5 | 5000 | 0.83 | 1/2000 |
|  | 2.5 | 6000 | 0.93 | 1/2400 |
|  | 5 | 500 | 0.72 | 1/100 |
|  | 5 | 600 | 0.73 | 1/120 |
|  | 5 | 800 | 0.75 | 1/160 |
|  | 5 | 1000 | 0.77 | 1/200 |
|  | 5 | 2000 | 0.87 | 1/400 |
|  | 5 | 3000 | 0.97 | 1/600 |
|  | 7.5 | 0 | 1.00 | — |
| A. niger 16404 - PDB | 0 | 10000 | 1.00 | — |
| (7 days) | 30 | 1000 | 0.70 | 1/33 |
|  | 30 | 2000 | 0.80 | 1/67 |
|  | 30 | 3000 | 0.90 | 1/100 |
|  | 50 | 0 | 1.00 | — |

The ratios of MBIT/sodium citrate tested ranged from 1/0.1 to 1/4000.

TABLE 54

First Component (A) = N-methyl-1,2-benzisothiazolin-3-one (MBIT)
Second Component (B) = Zinc pyrithione

| Microorganism | $Q_a$ | $Q_b$ | SI | A/B |
|---|---|---|---|---|
| E. coli 8739 - M9GY | 0 | 2 | 1.00 | — |
| (48 hours) | 2.5 | 0.4 | 0.45 | 1/0.2 |
|  | 2.5 | 0.5 | 0.50 | 1/0.2 |
|  | 2.5 | 0.6 | 0.55 | 1/0.2 |
|  | 2.5 | 0.8 | 0.65 | 1/0.3 |
|  | 2.5 | 1 | 0.75 | 1/0.4 |
|  | 5 | 0.3 | 0.65 | 1/0.06 |
|  | 5 | 0.4 | 0.70 | 1/0.08 |
|  | 5 | 0.5 | 0.75 | 1/0.1 |
|  | 5 | 0.6 | 0.80 | 1/0.1 |
|  | 5 | 0.8 | 0.90 | 1/0.2 |
|  | 7.5 | 0.3 | 0.90 | 1/0.04 |
|  | 7.5 | 0.4 | 0.95 | 1/0.05 |
|  | 10 | 0 | 1.00 | — |
| C. albicans 10231 - PDB | 0 | 30 | 1.00 | — |
| (72 hours) | 2.5 | 4 | 0.47 | 1/2 |
|  | 2.5 | 5 | 0.50 | 1/2 |
|  | 2.5 | 6 | 0.53 | 1/2 |
|  | 2.5 | 8 | 0.60 | 1/3 |
|  | 2.5 | 10 | 0.67 | 1/4 |

TABLE 54-continued

First Component (A) = N-methyl-1,2-benzisothiazolin-3-one (MBIT)
Second Component (B) = Zinc pyrithione

| Microorganism | $Q_a$ | $Q_b$ | SI | A/B |
|---|---|---|---|---|
| | 5 | 2 | 0.73 | 1/0.4 |
| | 5 | 3 | 0.77 | 1/0.6 |
| | 5 | 4 | 0.80 | 1/0.8 |
| | 5 | 5 | 0.83 | 1/1 |
| | 5 | 6 | 0.87 | 1/1 |
| | 5 | 8 | 0.93 | 1/2 |
| | 7.5 | 0 | 1.00 | — |
| A. niger 16404 - PDB (3 days) | 0 | 20 | 1.00 | — |
| | 20 | 5 | 0.75 | 1/3 |
| | 20 | 6 | 0.80 | 1/0.3 |
| | 20 | 8 | 0.90 | 1/0.4 |
| | 40 | 0 | 1.00 | — |

The ratios of MBIT/zinc pyrithione tested ranged from 1/0.001 to 1/400.

The invention claimed is:

1. A microbicidal composition consisting essentially of:
   (a) N-methyl-1,2-benzisothiazolin-3-one; and
   (b) at least one microbicide selected from among N-(n-butyl)-1,2-benzisothiazolin-3-one, and benzisothiazolinone, wherein a ratio of N-methyl-1,2-benzisothiazolin-3-one to N-(n-butyl)-1,2-benzisothiazolin-3-one is from 1:0.5 to 1:24, and a ratio of N-methyl-1,2-benzisothiazolin-3-one to benzisothiazolinone is from 1:0.3 to 1:20.

2. The composition of claim 1 in which said at least one microbicide comprises benzisothiazolinone.

3. A microbicidal composition consisting essentially of:
   (a) N-butyl-1,2-benzisothiazolin-3-one; and
   (b) benzisothiazolinone wherein a ratio of N-(n-butyl)-1,2-benzisothiazolin-3-one to benzisothiazolinone is from 1:0.02 to 1:16.

* * * * *